(12) United States Patent
Shusta et al.

(10) Patent No.: US 9,902,940 B2
(45) Date of Patent: *Feb. 27, 2018

(54) HUMAN BLOOD-BRAIN BARRIER ENDOTHELIAL CELLS DERIVED FROM PLURIPOTENT STEM CELLS AND BLOOD-BRAIN BARRIER MODEL THEREOF

(75) Inventors: Eric V. Shusta, Madison, WI (US); Samira Azarin, Madison, WI (US); Sean Palecek, Verona, WI (US); Ethan Lippmann, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 284 days.

This patent is subject to a terminal disclaimer.

(21) Appl. No.: 13/155,435

(22) Filed: Jun. 8, 2011

(65) Prior Publication Data
US 2012/0015395 A1  Jan. 19, 2012

Related U.S. Application Data

(60) Provisional application No. 61/355,901, filed on Jun. 17, 2010.

(51) Int. Cl.
*C12N 5/00* (2006.01)
*C12N 5/071* (2010.01)

(52) U.S. Cl.
CPC ........... *C12N 5/069* (2013.01); *C12N 5/0697* (2013.01); *C12N 2502/086* (2013.01); *C12N 2502/28* (2013.01); *C12N 2506/45* (2013.01); *C12N 2533/90* (2013.01)

(58) Field of Classification Search
CPC  C12N 2502/28; C12N 2506/45; C12N 5/069; C12N 5/0967
See application file for complete search history.

(56) References Cited

U.S. PATENT DOCUMENTS

| 8,293,495 | B2 * | 10/2012 | Shusta et al. | .................. 435/29 |
| 2008/0044847 | A1 * | 2/2008 | Shusta et al. | .................. 435/29 |
| 2011/0312018 | A1 |  12/2011 | Shusta et al. | |

FOREIGN PATENT DOCUMENTS

| WO | 2006056879 A1 | 6/2006 | |
| WO | WO 2006056879 | * 6/2006 | ............... C12N 5/06 |

OTHER PUBLICATIONS

Di et al, Eur J Med Chem 2003, 38:223-232.*
Filipczyk et al, Stem Cell Research, 2007, 1:45-60.*
Kubo et al, Blood, 2005, 105:4590-4597.*
Goldman et al, Stem Cells, 2009, 27:1750-1759.*
Levenberg et al, PNAS, 2002, 99:4391-4396.*
Garlanda et al, Arteriosclerosis, Thrombosis and Vascular Biology, 1997, 17:1193-1202.*
Lippmann et al, J Neurochem, 2011, 119:507-520.*
Park et al, PLoS ONE, 2012, 7:e37742.*
Kuchler-Bopp et al, NeuroReport ,1999, 10:1347-1353.*
Substrate Definition Google Search printout. www.google.com/search?q=substrate+definition&sourceid=ie7&ros=com. microsoft:e . . . pp. 1-2, preinted Sep. 1, 2015.*
Matrix definition (printout from google.com/search?q=matrix+definition&sourceid=ie7&rls=com. printed Feb. 25, 2016, pp. 1-2).*
Choi, et al., Hematopoietic and Endothelial Differentiation of Human Induced Pluripotent Stem Cells, Stem Cells, 2009, 27:559-567.
Cucullo, et al., Immortalized Human Brain Endothelial Cells and Flow-Based Vascular Modeling: A Marriage of Convenience for Rational Neurovascular Studies, Journal of Cerebral Blood Flow & Metabolism, 2008, 28:312-328.
Cullen, et al., GPR124, an Orphan G Protein-Coupled Receptor, is Required for CNS-Specific Vascularization and Establishment of the Blood-Brain Barrier, PNAS, 2011, 108(14):5759-5764.
Daadi, et al., Adherent Self-Renewable Human Embryonic Stem Cell-Derived Neural Stem Cell Line: Functional Engraftment in Experimental Stroke Model, PLoS ONE, 2008, 3(2):E1644, 9 pages.
Daneman, et al., Pericytes are Required for Blood-Brain Barrier Integrity During Embryogenesis, Nature, 2010, 468 (7323):562-566.
Deli, et al., Permeability Studies on In Vitro Blood-Brain Barrier Models: Physiology, Pathology, and Pharmacology, Cellular and Molecular Neurobiology, 2005, 25(1):59-127.
Forster, et al., Differential Effects of Hydrocortisone and TNFalpha on Tight Junction Proteins in an In Vitro Model of the Human Blood-Brain Barrier, Journal of Physiology, 2008, 586:1937-1949.
Goldman, et al., A Boost of BMP4 Accelerates the Commitment of Human Embryonic Stem Cells to the Endothelial Lineage, Stem Cells, 2009, 27:1750-1759.
James, et al., Expansion and Maintenance of Human Embryonic Stem Cell-Derived Endothelial Cells by TGFB Inhibition is Id1 Dependent, Nature Biotechnology, 2010, 28(2):161-166.
Kane, et al., Derivation of Endothelial Cells from Human Embryonic Stem Cells by Directed Differentiation, Analysis of MicroRNA and Angiogenesis In Vitro and In Vivo, Arterioscler Thromb Vasc Biol., 2010, 30:1389-1397.
Levenberg, et al., Endothelial Cells Derived from Human Embryonic Stem Cells, PNAS, 2002, 99(7):4391-4396.
Liebner, et al., Wnt/B-catenin Signaling Controls Development of the Blood-Brain Barrier, J. Cell Biol., 2008, 183 (3):409-417.
Nakahara, et al., High-Efficiency Production of Subculturable Vascular Endothelial Cells from Feeder-Free Human Embryonic Stem Cells Without Cell-Sorting Technique, Cloning and Stem Cells, 2009, 11(4):509-522.
Vodyanik, et al., Human Embryonic Stem Cell-Derived CD34+ Cells: Efficient Production in the Coculture with OP9 Stromal Cells and Analysis of Lymphohematopoietic Potential, Blood, 2005, 105(2):617-626.
Wang, et al., Endothelial and Hematopoietic Cell Fate of Human Embryonic Stem Cells Originates from Primitive Endothelium with Hemangioblastic Properties, Immunity, 2004, 21:31-41.

(Continued)

*Primary Examiner* — Marcia S Noble
(74) *Attorney, Agent, or Firm* — Quarles & Brady LLP

(57) ABSTRACT

A model blood brain barrier obtained from hPSCs is disclosed.

8 Claims, 17 Drawing Sheets
(15 of 17 Drawing Sheet(s) Filed in Color)

(56) References Cited

OTHER PUBLICATIONS

Wang, et al., Endothelial Cells Derived from Human Embryonic Stem Cells Form Durable Blood Vessels In Vivo, Nature Biotechnology, 2007, 25:317-318.
Weidenfeller, et al., Differentiating Embryonic Neural Progenitor Cells Induce Blood-Brain Barrier Properties, Journal of Neurochemistry, 2007, 101:555-565.
Ying, et al., Conversion of Embryonic Stem Cells into Neuroectodermal Precursors in Adherent Monoculture, Nature Biotechnology, 2003, 21:183-186.
PCT International Search Report and Written Opinion, PCT/US2011/039998, dated Feb. 10, 2012.
Stins, et al., "Selective expression of adhesion molecules on human brain microvascular endothelial cells", Journal of Neuroimmunology 76, (1997), pp. 81-90.
Wong, et al., "Upregulation of intercellular adhesion molecule-1 (1CAM-1) expression in primary cultures of human brain microvessel endothelial cells by cytokines and lipopolysaccharide", Journal of Neuroimmunology, 39 (1992) pp. 11-22.
European Patent Office Communication for Application No. 11743384.7 dated May 19, 2014.

\* cited by examiner

SEQUENCE LISTING

```
<160> NUMBER OF SEQ ID NOS: 64

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
caccgtcaag gctgagaacg                                               20

<210> SEQ ID NO 2
<211> LENGTH: 20
```

```
<212> TYPE: DNA
<213> ORGANISM: Artificial Sequence
<220> FEATURE:
<223> OTHER INFORMATION: Synthetic oligonucleotide

<400> SEQUENCE: 2
gccccacttg attttggagg                                                    20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
acgctctgat ccctctcagt                                                    20

<210> SEQ ID NO 4
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 4
gcagtacaca ccgatgatga ag                                                 22

<210> SEQ ID NO 5
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 5
tgaatctgga ggaagacatg ac                                                 22

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6
ccaggcacca aaatgaaacc                                                    20

<210> SEQ ID NO 7
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 7
cagatgtcaa ctccaaacaa gg                                                 22

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 8
```

```
gatgggatat acaggctgac c                                              21

<210> SEQ ID NO 9
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 9
tttggaatcg tgctctccg                                                 19

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
aaggtgagta agcaggacaa g                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
tacctcacaa aaccccatc c                                               21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12
ggctgtataa gccagcatca t                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 13
tcgtcagtac catatcccat g                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 14
cccattctgt gcatgtcttt t                                              21

<210> SEQ ID NO 15
<211> LENGTH: 19
<212> TYPE: DNA
<213> ORGANISM: Artificial Sequence
```

```
<220> FEATURE:
<223> OTHER INFORMATION: Synthetic oligonucleotide

<400> SEQUENCE: 15
gatgataacg gcgatgtga                                            19

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 16
aacaaagcag ccaccgcaga c                                         21

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17
gttcatggag gaccgcagtg                                           20

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
tcttcttgtt cattcggcat t                                         21

<210> SEQ ID NO 19
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 19
ggagtcacag tgccatcaca t                                         21

<210> SEQ ID NO 20
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 20
cctgacctta cttcacagcc t                                         21

<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 21
cgcaatagac aaggacataa cac                                       23
```

```
<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22
ggtcaaactg cccatacttg                                              20

<210> SEQ ID NO 23
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 23
cccgaaaggc caggtgta                                                18

<210> SEQ ID NO 24
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 24
agcaagcttc cggggact                                                18

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25
gccattgtcg tctttatgtc                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26
aaacacatac ccatcaacga                                              20

<210> SEQ ID NO 27
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 27
ttaaagtaga tcacctcctc ga                                           22

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide
```

```
<400> SEQUENCE: 28
ggatgagatt cgtaccagag                                             20

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 29
ggtgtttctt agtagttatg gg                                          22

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30
tcttattggc tttgtgttgg                                             20

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 31
tgttcatcct ctgattctct g                                           21

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32
gcttagatgt tcccaaagtc                                             20

<210> SEQ ID NO 33
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 33
ggaaatcaca cgaaattcac                                             20

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
gcacgatatt tactttgctc                                             20

<210> SEQ ID NO 35
```

```
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 35
gctttcctta cctctaaaca g                                              21

<210> SEQ ID NO 36
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 36
gaaggtgata gaactgagcg                                                20

<210> SEQ ID NO 37
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 37
tgtcagtgtt caacctcag                                                 19

<210> SEQ ID NO 38
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 38
gtggatggag taggacga                                                  18

<210> SEQ ID NO 39
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 39
gttattctag gtattgtgct gg                                             22

<210> SEQ ID NO 40
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 40
ctgatgagat ctaacatggc                                                20

<210> SEQ ID NO 41
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 41
```
aatagaagtg ttgggctgag                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 42
cgagacacct taaagaacag                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 43
atataagaag gcattgaccc                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 44
atctgtagaa cacttgacca                                               20

<210> SEQ ID NO 45
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 45
aatctacaac tcggagtcca                                               20

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 46
caagcctctg aatgtaaatc c                                             21

<210> SEQ ID NO 47
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 47
tcactacatt aagactctgt cc                                            22

<210> SEQ ID NO 48
<211> LENGTH: 23
<212> TYPE: DNA

<213> ORGANISM: Artificial Sequence
<220> FEATURE:
<223> OTHER INFORMATION: Synthetic oligonucleotide

<400> SEQUENCE: 48
ggatactttc tttaggacga gag                                              23

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 49
gtagattctg cctctgaact c                                                21

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 50
cttcacagat actcccttct c                                                21

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
aaagatgtgg aagtagagga                                                  20

<210> SEQ ID NO 52
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 52
atgcttagga gaattgacac                                                  20

<210> SEQ ID NO 53
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 53
caatgcagag atcaattcaa gg                                               22

<210> SEQ ID NO 54
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 54
acgctttcct tatccttagt g                                                21

<210> SEQ ID NO 55
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 55
gcacagctct cctattgaaa c                                              21

<210> SEQ ID NO 56
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 56
ggtatccctc tagccattca g                                              21

<210> SEQ ID NO 57
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 57
gactacattg aatttgccag cc                                             22

<210> SEQ ID NO 58
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 58
tcttgtgggc tcggttaatg                                                20

<210> SEQ ID NO 59
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 59
cgggagatca agcagaatg                                                 19

<210> SEQ ID NO 60
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 60
cgtggcactt acattccag                                                 19

<210> SEQ ID NO 61
<211> LENGTH: 18
<212> TYPE: DNA
<213> ORGANISM: Artificial Sequence
<220> FEATURE:

```
<223> OTHER INFORMATION: Synthetic oligonucleotide

<400> SEQUENCE: 61
gcttcgtcaa gtgcaaca                                                 18

<210> SEQ ID NO 62
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 62
ggagtggatg tgcaaaatg                                                19

<210> SEQ ID NO 63
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 63
tggaacagaa tagttgaggg ct                                            22

<210> SEQ ID NO 64
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 64
agccaaggga cagtgcgagt gt                                            22
```

HUMAN BLOOD-BRAIN BARRIER ENDOTHELIAL CELLS DERIVED FROM PLURIPOTENT STEM CELLS AND BLOOD-BRAIN BARRIER MODEL THEREOF

CROSS-REFERENCE TO RELATED APPLICATION

This application claims priority to U.S. provisional application 61/355,901 filed Jun. 17, 2010, which is incorporated by reference herein.

STATEMENT OF FEDERALLY SPONSORED RESEARCH

This invention was made with government support under NS052649 awarded by the National Institutes of Health. The government has certain rights in the invention.

BACKGROUND OF THE INVENTION

The blood-brain barrier (BBB) is composed of specialized brain microvascular endothelial cells (BMECs) that help regulate the flow of substances into and out of the brain. Intercellular tight junctions limit the passive diffusion of molecules into the brain and result in blood vessels exhibiting extremely high trans-endothelial electrical resistance (TEER) in vivo[1]. In addition, efflux transporters including p-glycoprotein contribute to the barrier properties by returning small lipophilic molecules capable of diffusing into BMECs back to the bloodstream. As a result, BMECs are endowed with a requisite network of specific transport systems to shuttle essential nutrients and metabolites across the BBB. In addition, because of its substantial barrier properties, the BBB has significantly hampered neuropharmaceutical development by preventing uptake of the majority of small molecule pharmaceuticals and essentially all biologics[2]. Conversely, breakdown and dysfunction of the BBB is associated with a variety of neurological diseases, including Alzheimer's disease, stroke, multiple sclerosis, and brain tumors[3]. These issues have collectively led researchers to develop a variety of BBB models to enable detailed mechanistic studies in vitro.

Most in vitro BBB models have been established using brain microvessels isolated from primary animal sources such as cow, pig, rat and mouse[4]. However, as a result of inevitable species differences[5,6], a robust in vitro BBB model of human origin would be of high utility for conducting high-throughput screening for brain-penetrating molecules or for study of BBB developmental, regulatory, and disease pathways in humans.

Previously, human BBB models have been established by culturing primary human BMECs isolated from autopsy tissue or, more often, freshly resected brain specimens derived from brain tumor or epilepsy patients. As a result, issues involving BMEC availability and fidelity limit the universal use of these human BBB models[7]. As another route toward a human BBB model, human BMECs have been immortalized[8]. However, immortalized BMECs suffer from poor barrier properties, including low baseline TEER[9,10] and discontinuous tight junction protein expression[8], which are key hallmarks of the in vivo BBB. Collectively, these previous models have facilitated initial studies of human brain endothelium but fall short of the necessary criteria to establish a robust human in vitro BBB model.

Needed in the art is an improved BBB model.

SUMMARY OF THE INVENTION

In one embodiment, the present invention is a method of producing brain specific endothelial cells, preferably comprising the steps of growing human pluripotent stem cells (hPSCs) on a surface, inducing differentiation of the cells by culturing the cells in unconditioned medium, wherein no fibroblast growth factor (FGF) is present and wherein endothelial cell (EC) regions of the cultures are observed, and expanding the EC regions by culturing the cells in EC medium, wherein the expanded cells are GLUT-1$^+$, PECAM-1$^+$, claudin-5$^+$, occludin$^+$, ZO-1$^+$ and p-glycoprotein$^+$. Preferably, the expanded cells are grown on a surface comprising extracellular matrix proteins and are von Willebrand factor$^+$ and VE-cadherin$^+$. Preferably, the hPSCs are selected from the group consisting of human embryonic stem cells and induced pluripotent stem cells. In a preferred embodiment, the hPSCs are derived from a human patient.

In a preferred embodiment, the method additionally comprises the step of co-culturing the expanded cells, which are GLUT-1$^+$, PECAM-1$^+$, claudin-5$^+$, occludin$^+$, ZO-1$^+$ and p-glycoprotein$^+$, with a cell-type selected from the group of astrocytes, neurons, neural progenitor cells and pericytes. In one embodiment, the co-culturing is with at least two cell types from the group.

Preferably, the method additionally comprises the step of growing the expanded cells, which are GLUT-1$^+$, PECAM-1$^+$, claudin-5$^+$, occludin$^+$, ZO-1$^+$ and p-glycoprotein$^+$, to confluence, wherein a blood brain barrier model is obtained. Most preferably, the expanded cells are grown on solid support. In a preferred embodiment, the method comprises the step of taking an initial TEER measurement of the confluent cells, wherein the TEER measurement is between 100-300 $\Omega \times cm^2$. In another preferred embodiment, the method comprises the step of taking a TEER measurement, wherein the TEER measurement is between 300-800 $\Omega \times cm^2$. In yet another preferred embodiment, the method comprises the step of taking a TEER measurement, wherein the TEER measurement is between 800-3000 $\Omega \times cm^2$.

In another embodiment, the present invention is a cell population produced by growing human pluripotent stem cells (hPSCs) on a surface, inducing differentiation of the cells by culturing the cells in unconditioned medium, wherein no fibroblast growth factor (FGF) is present and wherein endothelial cell (EC) regions of the cultures are observed, and expanding the EC regions by culturing the cells in EC medium, wherein the expanded cells are GLUT-1$^+$, PECAM-1$^+$, claudin-5$^+$, occludin$^+$, ZO-1$^+$ and p-glycoprotein$^+$. Preferably, the cells are seeded onto a solid surface coated with extracellular matrix proteins.

In yet another embodiment, the present invention is a cell population produced by growing human pluripotent stem cells (hPSCs) on a surface, inducing differentiation of the cells by culturing the cells in unconditioned medium, wherein no fibroblast growth factor (FGF) is present and wherein endothelial cell (EC) regions of the cultures are observed, expanding the EC regions by culturing the cells in EC medium, wherein the expanded cells are GLUT-1$^+$, PECAM-1$^+$, claudin-5$^+$, occludin$^+$, ZO-1$^+$ and p-glycoprotein$^+$ and co-culturing the expanded cells with a cell-type selected from the group of astrocytes, neurons, neural progenitor cells and pericytes. Preferably, the cells are seeded onto a solid surface coated with extracellular matrix proteins.

In yet another embodiment, the present invention is an in vitro cell culture of brain specific endothelial cells, wherein the cells are GLUT-1+, PECAM-1+, claudin-5+, occludin+, ZO-1+ and p-glycoprotein+ and wherein the cells are derived from hPSCs. Preferably, the cells are grown to confluence on a solid support and are von Willebrand factor+ and VE-cadherin+, such that a blood brain barrier is obtained. Preferably, the cells also express LDLR, LRP1, INSR, LEPR, BCAM, TFRC and AGER. Most preferably, the cells additionally express STRA6, SLC7A5, SLC1A1, SLC38A5 and SLC16A1. In a most preferred embodiment, the cells also additionally express ABCB1 and ABCG2. Preferably, the cells are grown to confluence on a solid support, wherein a blood brain barrier is obtained. Preferably, the initial TEER measurement of the cells is between 100-300 Ω×cm$^2$. Most preferably, the cells have been co-cultured with a cell-type selected from the group of astrocytes, neurons, neural progenitor cells and pericytes. In another preferred embodiment, the TEER measurement is between 300-800 Ω×cm$^2$. In yet another preferred embodiment, the TEER measurement is between 800-3000 Ω×cm$^2$.

In yet another embodiment, the present invention is a method of determining whether a blood brain barrier model is permeable to a test compound, cell or protein, comprising the steps of exposing a test compound, cell or protein to the blood brain barrier (BBB) model and examining the permeability of the test compound, wherein the BBB model is produced by growing human pluripotent stem cells (hPSCs) on a surface, inducing differentiation of the cells by culturing the cells in unconditioned medium, wherein no fibroblast growth factor (FGF) is present and wherein endothelial cell (EC) regions of the cultures are observed, expanding the EC regions by culturing the cells in EC medium, wherein the expanded cells are GLUT-1+, PECAM-1+, claudin-5+, occludin+, ZO-1+ and p-glycoprotein+, and growing the ECs to confluence. In a preferred embodiment, the method additionally comprises the step of exposing the model to a second test compound and determining whether the second compound is an inhibitor or agonist of influx or efflux.

In yet another embodiment, the present invention is a method of determining whether a blood brain barrier model is permeable to a test compound, cell or protein, comprising the steps of exposing a test compound, cell or protein to the blood brain barrier (BBB) model and examining the permeability of the test compound, wherein the BBB model is produced by growing human pluripotent stem cells (hPSCs) on a surface, inducing differentiation of the cells by culturing the cells in unconditioned medium, wherein no fibroblast growth factor (FGF) is present and wherein endothelial cell (EC) regions of the cultures are observed, expanding the EC regions by culturing the cells in EC medium, wherein the expanded cells are GLUT-1+, PECAM-1+, claudin-5+, occludin+, ZO-1+ and p-glycoprotein+, and co-culturing the expanded ECs with a cell-type selected from the group of astrocytes, neurons, neural progenitor cells, and pericytes. In a preferred embodiment, the method additionally comprises the step of exposing the model to a second test compound and determining whether the second compound is an inhibitor or agonist of influx or efflux.

In yet another embodiment, the present invention is a method of determining whether a blood brain barrier model is permeable to a test compound, cell or protein, comprising the steps of exposing a test compound, cell or protein to the blood brain barrier (BBB) model and examining the permeability of the test compound, wherein the BBB model is produced by growing an in vitro culture of brain specific endothelial cells to confluence on a solid support, wherein the cells are derived from hPSCs and are GLUT-1+, PECAM-1+, claudin-5+, occludin+, ZO-1+, p-glycoprotein+, von Willebrand factor+ and VE-cadherin+. In a preferred embodiment, the method additionally comprises the step of exposing the model to a second test compound and determining whether the second compound is an inhibitor or agonist of influx or efflux.

DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

To create a robust, scalable human BBB model, we sought to take advantage of the in vitro developmental potential of human pluripotent stem cells (hPSCs). We report below a facile hPSC differentiation method capable of reproducibly generating pure populations of endothelial cells possessing BBB properties that in turn provide a high-fidelity human in vitro BBB model.

hPSCs, including both human embryonic stem cells (hESCs)[11] and induced pluripotent stem cells (iPSCs)[12, 13], exhibit virtually unlimited self-renewal and the capacity to differentiate into somatic cell types from all three embryonic germ layers. While human endothelial cells (ECs) have been generated from hPSCs by a variety of methods, including embryoid body differentiation[14-18] and OP9 stromal cell co-culture[19, 20], ECs are known to develop distinct gene and protein expression profiles that depend on microenvironment cues during organogenesis[21] (see Table 9), and hPSC-derived ECs with organ-specific properties have yet to be reported.

In vivo, BBB specification begins as ECs forming the perineural vascular plexus invade an embryonic brain microenvironment comprised of neuroepithelial cells, radial glia, neuroblasts and neurons. Notably much of this early BBB induction occurs in the absence of astrocytes[22-25]. The cells of the developing embryonic brain provide relevant molecular cues, such as Wnt7a and Wnt7b, to help drive the BBB specification of ECs[26, 27]. Thus, we hypothesized that a strategy, which simultaneously co-differentiates hPSCs to both neural and endothelial lineages, could result in hPSC-derived ECs possessing BBB attributes.

Figure 1:
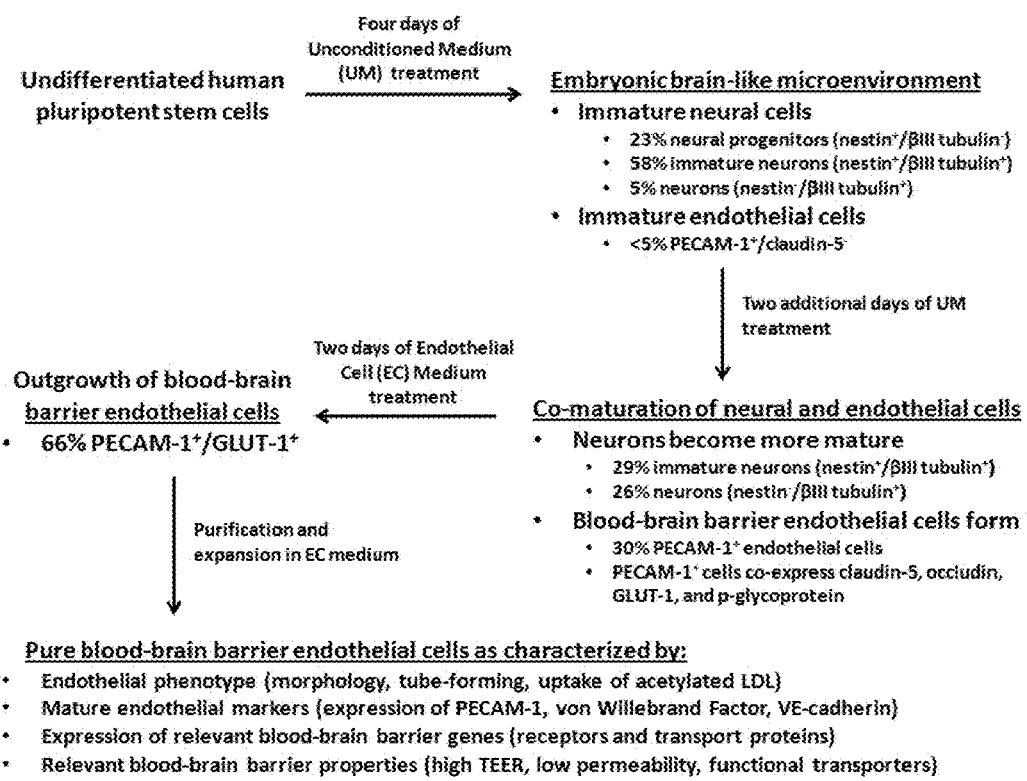
FIG. 1 summarizes a preferred embodiment of the present invention. Briefly, differentiation from human pluripotent stem cells (hPSCs) is induced by treating hPSCs with unconditioned medium (UM). After 3-4 days in UM, embryonic brain-like microenvironment start to form and very small clusters of cells with endothelial cell (EC) morphology are observable. After another two days in UM, ECs are more readily observed as large patches and neurons become more mature. EC medium is added at this point and BBB ECs (characterized as PECAM-1+/GLUT-1+) are expanded. After two days in EC medium, at least 65% of the cells are ECs.

A preferred embodiment of the method of the present invention is described in FIG. 1. In general, the method of the present invention has the following steps:

(1) Human pluripotent stem cells (hPSCs) are grown on suitable matrix, preferably MATRIGEL-coated plates. hPSCs include both hESCs and iPSCs. hESCs can be derived from blastocyst or morula stage embryos. Methods for deriving hESCs from blastocyst and culturing them are well known in the art[11, 76, 85, 86, 102]. A preferred feeder-independent method can be found in reference 68. iPSCs are somatic cells reprogrammed by genetic and/or chemical factors. Methods for isolating somatic cells and reprogramming them to be iPSCs are also well known in the art[12, 13, 69-75, 79-84, 87-94, 96-101, 103, 104, 118-120]. One may also wish to use established hESC and iPSC lines. Many cell lines other than the ones tested in the Examples below are available[68, 69-104, 118-121].

MATRIGEL is a mixture of extracellular matrix proteins and growth factors derived from Engelberth-Holm-Swarm tumor basement membranes. MATRIGEL could be replaced with any matrix that presents the necessary combination of growth factors and matrix proteins[60, 61, 62]. (For an overview of the various extracellular matrices and growth factors that are sufficient for maintaining hPSCs, see reference 63.) The plates are placed in a defined medium, preferably mTeSR1 or TeSR[32]. Because this media is just used for the expansion of the cells prior to differentiation, any defined medium that supports hPSC growth could substitute. This growth is typically between 2-3 days to allow colony attachment and growth. At this point, the cells are at approximately 20-30% confluence.

(2) To induce differentiation, the colonies are then subjected to an unconditioned media (UM). Unconditioned medium refers to the lack of conditioning by mouse fibroblast feeders or other feeder cells. UM is used to induce differentiation while conditioned media (CM) is used to maintain cells in the undifferentiated state.

A typical UM is Dulbecco's Modified Eagle's Medium/Ham's F12 (Invitrogen) containing 20% Knockout Serum Replacer (Invitrogen), 1×MEM nonessential amino acids (Invitrogen), 1 mM L-glutamine (Sigma), 0.1 mM β-mercaptoethanol. There is no FGF in the media because FGF promotes self-renewal of hPSCs. After 3-4 days in UM, EC regions are observed. EC regions are very small clusters of cells with EC morphology which are observable by light microscopy (See FIG. 2e). A "Cobblestone" morphology probably best describes the EC morphology. EC morphology is also characterized by high levels of cell-cell interaction and, typically, by contact-inhibited monolayer growth.

Suitable cells can be also characterized immunocytochemically as PECAM-1+ with weak expression of GLUT-1 and lacking expression of claudin-5.

(3) After 5-7 days of UM treatment, the EC regions of the pluripotent stem cell cultures are more readily observed as large patches. (See FIG. 2f for representative image). EC medium is then added. Typically, EC medium consists of human endothelial serum-free medium (Invitrogen) supplemented with 1% platelet-poor plasma-derived serum (Biomedical Technologies Inc) and 20 ng/mL bFGF. In general, EC medium can be any medium which selectively expand the EC regions.

(4) Following 1-2 days of EC medium treatment, the expanded EC regions are typically probed with antibodies against BBB markers. The combination of tight junction proteins claudin-5 and occludin[64], along with the glucose transport isoform GLUT-1[65] and efflux transporter p-glycoprotein[66], are often used to define ECs characteristic of the blood-brain barrier. All such antibodies are commercially available (Invitrogen and Thermo Fisher).

(5) Flow cytometry may be utilized to quantify the development of the cells. After 4 days of UM treatment, no significant PECAM-1+ population will be detected. GLUT-1 expression will be at the limit of detection. Following 6 days of UM treatment, a population expressing high levels of GLUT-1 is detected at approximately 30%. The PECAM-1+ population is also evident at approximately 36%. After switching the cultures to EC medium for one day, the GLUT-1 population will increase slightly to 36% but then increase dramatically to 66% after another day. At this point, essentially 100% of the PECAM-1+ cells are also GLUT-1 positive. (See Results section 1 below, for description of these phenomena.)

(6) In order to test for blood brain barrier phenotype and functionality, one would first provide the signals necessary for further maturation of the pluripotent stem cell-derived BMECs. Typically, colonies of the pluripotent stem cell-derived ECs at approximately 6 days of UM and approximately 2 days of EC medium treatment are dissociated and plated onto fibronectin/collagen IV-coated tissue culture plates in EC medium. (In the examples below, we add the coating ourselves to standard tissue culture treated polystyrene, but a suitable surface could be any surface coated with appropriate EC matrix proteins, of which fibronectin/collagen IV are typical ones for BMEC.) The cells will grow to confluence after 1-2 days, depending on the initial seeding density, and show characteristic EC morphology. (The Examples below describe characteristic EC morphology.) Immunocytochemical analysis will demonstrate that the tight junctions in the pluripotent stem cell-derived BMEC monolayer will remain intact after subculture.

(7) To examine tight junction expression and the TEER value, one may seed the pluripotent stem cell-derived BMECs onto TRANSWELL™ filters coated with fibronectin/collagen IV matrix and grow to confluence in EC media. Initial TEER measurements taken at confluence will range from 100-300 $\Omega \times cm^2$. These values are consistent with other primary in vitro models from various species[4, 34] and are well above measurements observed in peripheral non-brain ECs (2-30 $\Omega \times cm^2$). Importantly, TEER was increased significantly by co-culture with astrocytes, which is a hallmark of primary cultured BMECs[67]. After 24 hours of co-culture with primary rat astrocytes, we were able to achieve a maximum TEER value of 1450±140 $\Omega \times cm^2$. Even in the absence of astrocyte induction, the confluent BMECs can reach 800 Ω×cm² after 24 hours. The in vivo BBB has been measured to be between 1000-3000 Ω×cm² (see reference 1).

Typically, one would co-culture hPSC-derived BMECs with astrocytes as below. Preferably, one would use human cells. There are similarities in culture of all mammalian astrocyte cells. For rat astrocyte isolation, cortices were isolated from P6 neonatal Sprague Dawley rats (Harlan) and minced in Hank's Balanced Salt Solution (HBSS; Sigma). This tissue was digested in HBSS containing 0.5 mg/mL trypsin (Mediatech, Inc.) in a 37° C. shaker bath for 25 min, followed by digestion in HBSS containing 114 U/mL DNase I (Worthington Biochemical) in a 37° C. shaker bath for 5 min. After trituration and filtration, cells were cultured on collagen-I-coated flasks (100 μg/mL; Sigma) in DMEM containing 10% qualified heat-inactivated fetal bovine serum (FBS; Invitrogen), 10% heat-inactivated horse serum (Sigma), 2 mM L-glutamine, and 1% antibiotic-antimycotic (Invitrogen).

Astrocytes grow to confluence after 7-10 days in culture, at which point they can be frozen if desired. Rodent astrocytes can be used for co-culture anywhere from 7-21 days after their initial isolation, or frozen stocks can be thawed and re-grown to confluence and used in the same time frame.

Astrocytes can also be differentiated from either primary rodent or human NPCs (such as those derived in Clive Svendsen's lab[122], whereas one would expect NPC-derived astrocytes to be appropriately mature after 9-15 days of differentiation.

Additionally, one could use hPSC-derived astrocytes[123] in place of NPC-derived astrocytes. Co-cultures with astrocytes are initiated when hPSC-derived BMECs reach confluence and maximum TEER is achieved after 24 hours. One can also use astrocyte-conditioned medium rather than direct co-culture or may add chemical factors that mimic this medium.

"Initial TEER measurements at confluence" refers to cells seeded on a TRANSWELL™ filter. After 24 hours on this same filter, the TEER can reach 800 Ω×cm². Cultures must be examined by eye to determine confluency. Thus, at initial onset of confluency, TEER may be 100 Ω×cm², but if TEER is measured 6 hours after confluency was truly completed, it may read as 300 Ω×cm².

Figure 4:
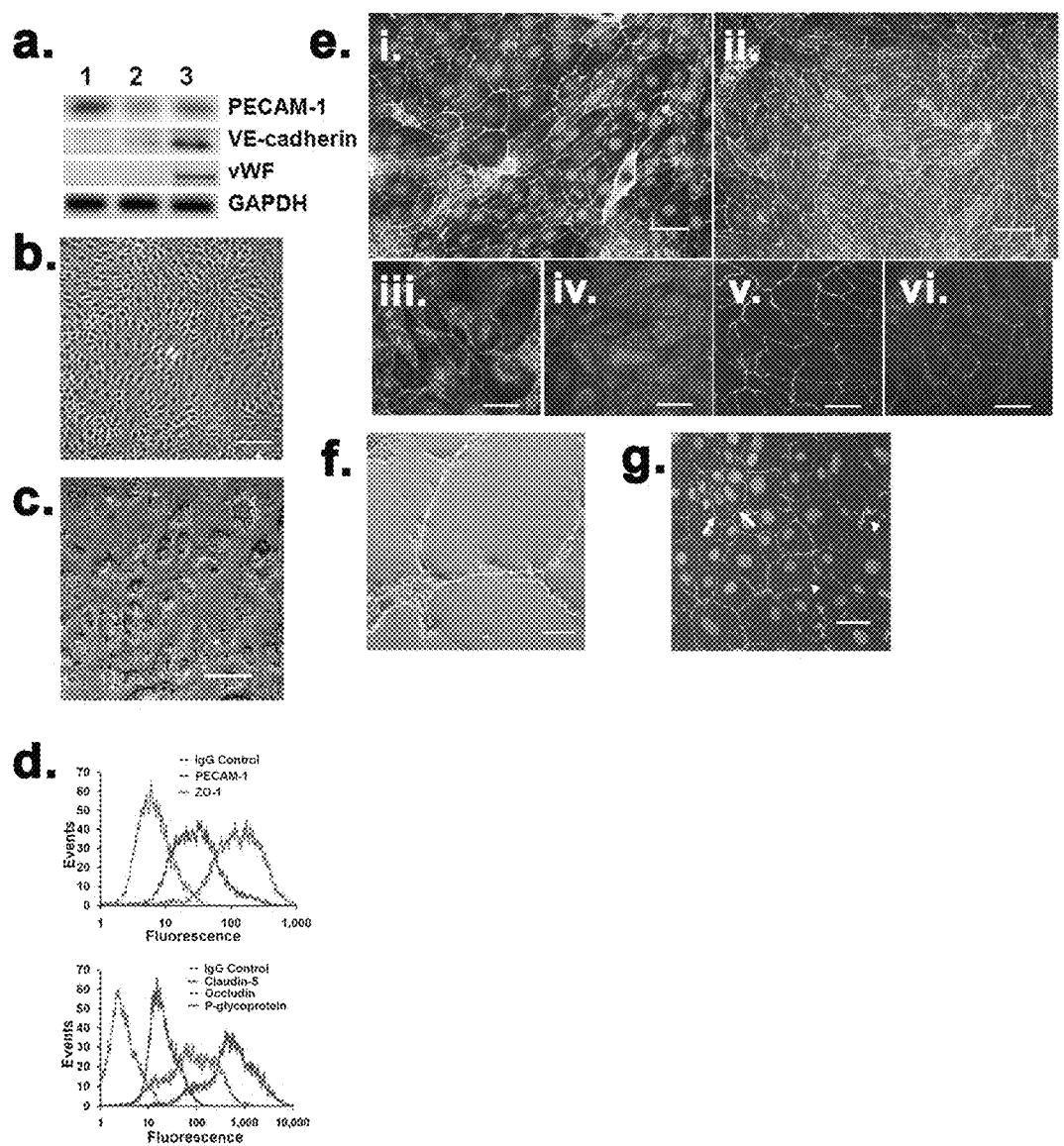
FIG. 4 shows purification of iPSC-derived BMECs on collagen/fibronectin matrix. (a) Gel electrophoresis of PCR products for transcripts encoding PECAM-1, VE-cadherin, and von Willebrand Factor (vWF) in differentiating IMR90-4 iPS cells after 3 days of differentiation in UM (lane 1), 6 days in UM and 2 days in EC medium (lane 2), or subculture onto a collagen/fibronectin matrix for 2 days (lane 3). (b) Phase contrast image of IMR90-4-derived BMECs on the collagen/fibronectin matrix. Scale bar indicates 100 μm. (c) Acetylated LDL uptake in IMR90-4-derived BMECs. Scale bar indicates 50 μm. (d) Flow cytometry demonstrates purity of IMR90-4-derived BMECs after subculture. ZO-1 and PECAM-1 expression are compared to the appropriate rabbit IgG control, and occludin, claudin-5, and p-glycoprotein expression are compared to the appropriate mouse IgG control. (e) Characteristic BBB markers remain after purification of IMR90-4-derived BMECs. PECAM-1 (i, red) is shown co-localized with claudin-5 (green) and DAPI nuclear stain (blue). vWF expression is demonstrated (ii, red) with occludin (green) and DAPI (blue). GLUT-1 (iii), p-glycoprotein (iv), and ZO-1 (v), and VE-cadherin (vi) are also observed. Scale bars indicate 50 μm. (f) Seeding of purified IMR90-4-derived BMECs onto Matrigel in the presence of 40 ng/mL VEGF leads to vascular tube formation. Scale bar indicates 100 μm. In the absence of VEGF, cells did not form tubes (data not shown). (g) Subculture prior to full differentiation leads to a defective BBB phenotype. Differentiating IMR90-4 cultures purified on the collagen/fibronectin matrix after only 4 days of UM treatment do not grow to confluence and areas with malformed or discontinuous claudin-5 expression (green) are readily observed. Co-label with DAPI is shown (blue). Arrows highlight continuous claudin-5 expression while arrowheads indicate defective claudin-5. Scale bar indicates 50 μm.

The hPSC-derived BMECs of the present invention could be used (1) on their own in monoculture, (2) in co-culture with rat/mouse/human astrocytes and/or neurons and/or pericytes, (3) in co-culture with astrocyte/neuron cell lines, or (4) in co-culture with NPC or NPC-derived astrocytes/neurons. Monoculture would be useful in studies of BBB development—the hPSC-derived BMECs are developed in the absence of astrocytes, thus gene/protein expression in monoculture BMECs could be compared to BMECs co-cultured with astrocytes, neurons, and/or pericytes to identify potential signaling pathways that are regulated specifically by these brain cell types. Moreover, because co-culture with one or more brain cell types has been shown to enhance TEER and be more representative of the in vivo BBB[111-116] (also see data in Examples). This condition would be preferably used for permeability screens, although one could use the monoculture condition for this purpose, but it may not necessarily represent the BBB as accurately (see FIG. 4, for example).

The present invention is also a population of brain specific endothelial cells (BMECs) with the following characteristics: (1) The cells preferably exhibit endothelial markers PECAM-1, VE-cadherin and von Willebrand Factor, tight junction proteins claudin-5, occludin and ZO-1, and transport proteins GLUT-1, p-glycoprotein, BCRP and the MRP family. (2) Additionally, when grown to confluence in EC media, initial TEER measurements taken at confluence range between 100 to 300 $\Omega \times c^{m2}$. Later TEER measurements (see Examples) may be between 300-800 Ω×cm² or between 800-3000 Ω×cm².

These TEER values also correspond to low permeability to the BBB-impermeant small molecule sodium fluorescein ($2.2 \pm 0.1 \times 10^{-6}$ cm/min). (3) Finally, when being exposed to neural cues, the cells express at least 4 of receptors/transporters listed in Table 1 below. All are typical/important and are indicators of the fidelity of the BBB properties of the model. Most important for drug transport studies is the ABC transporters. Note the absence of PLVAP, as that absence is indicative of BBB compared with peripheral or "general" endothelial cells.

TABLE 1

Genes expressed and/or highly enriched at the blood-brain barrier

| Gene | Expressed by hPSC-derived blood-brain barrier endothelium? |
|---|---|
| LDLR (low density lipoprotein receptor) | Yes |
| LRP1 (low-density lipoprotein receptor-related protein 1) | Yes |
| INSR (insulin receptor) | Yes |
| LEPR (leptin receptor) | Yes |
| BCAM (lutheran glycoprotein) | Yes |
| TFRC (transferrin receptor) | Yes |
| AGER (receptor for advanced glycation endproducts) | Yes |
| STRA6 (retinol binding protein) | Yes |
| SLC7A5 (LAT1) | Yes |
| SLC1A1 (EAAT3) | Yes |
| SLC38A5 (SNAT5) | Yes |
| SLC16A1 (MCT1) | Yes |
| ABCB1 (p-glycoprotein) | Yes |
| ABCG2 (breast cancer resistance protein) | Yes |
| ABCC1 (MRP1) | Yes |
| ABCC2 (MRP2) | Yes |
| ABCC4 (MRP4) | Yes |
| ABCC5 (MRP5) | Yes |

The cell populations of the present invention are useful in several general commercial and research settings. When seeded and grown on a TRANSWELL™ filter, the cells could be used for permeability screening. To conduct a typical permeability screen, one would add the compound of interest to the apical side of the filter (above the endothelial cells). One would then measure the accumulation of this compound in the basolateral chamber (below the endothelial cells) over a given time period. Relative transport of this compound through the endothelial monolayer can then be benchmarked against other reference compounds that are known to readily penetrate the BBB (e.g. diazepam) or be excluded by the BBB (e.g. insulin, sucrose) to determine whether the compound of interest is a possible candidate for delivery across the BBB. Conversely, similar experiments could be used to identify peripheral-acting drugs that do not cross the BBB appreciably so as to limit brain toxicity of said compounds.

In another embodiment, potential inhibitors/agonists of various BBB efflux and influx systems could be screened using the hPSC-derived BMEC model to find modulators of BBB uptake and clearance. Note FIGS. 5e and 5f as examples of these types of study. Details are given in the Methods section of the Examples.

In a mono-layer form or in solution if released from a surface, the cells would be useful for toxicity screening. One may wish to do scientific studies on TRANSWELL™ inserts, plates, or phase-type experiments in solutions as described above.

Additionally, one may wish to create patient-specific BMECs and BBB models by isolating cells from a patient and creating hPSCs from these cells. To create patient-specific BMECs one would use iPSC lines derived from a patient. The patient would typically have a genetic disorder that would give rise to the disease one wishes to study. For example, iPSC lines have been derived from patients with ALS[105] and spinal muscular atrophy[106]. Disease-specific iPSCs have also been generated from patients with adenosine deaminase deficiency-related severe combined immunodeficiency (ADA-SCID), Shwachman-Bodian-Diamond syndrome (SBDS), Gaucher disease (GD) type III, Duchenne (DMD) and Becker muscular dystrophy (BMD), Parkinson disease (PD), Huntington disease (HD), juvenile-onset type 1 diabetes mellitus (JDM), Down syndrome (DS)/trisomy 21, the carrier state of Lesch-Nyhan syndrome, Fanconi anemia, various myeloproliferative disorders, and dyskeratosis congenita[99, 107-110].

In another embodiment, the present invention is a method of examining the ability of a compound to cross a model blood brain barrier comprising the steps of creating a confluent cell population, as described above, and determining whether the model blood brain barrier is a barrier to compound movement. One may examine US 2008/0044847, Blood Brain Barrier Model, for a typical version of use of a BBB Model for testing in a typical analysis of results.

EXAMPLES

In General

The blood-brain barrier (BBB) plays an important role in maintaining brain health and is often compromised in disease. Moreover, as a result of its significant barrier properties, this endothelial interface restricts uptake of neurotherapeutics. As such, a renewable source of human BBB endothelium could prove enabling for brain research and pharmaceutical development. Herein, we demonstrate that endothelial cells generated from human pluripotent stem cells (hPSCs) can be specified to possess many BBB attributes, including well-organized tight junctions, polarized efflux transporter activity, and expression of nutrient transporters. Importantly, these hPSC-derived BBB endothelial cells respond to astrocytic cues yielding very tight barrier properties as measured by transendothelial electrical resistance (1450±140 $\Omega \times cm^2$) while exhibiting molecular permeability that correlates well with in vivo brain uptake. Moreover, specification of hPSC-derived BBB endothelial cells occurs in concert with neural cell co-differentiation via Wnt/β-catenin signaling, consistent with previous transgenic rodent studies. Taken together, this study represents the first example of organ-specific endothelial differentiation from hPSCs.

A Novel Strategy for Differentiation of hPSCs into BBB Endothelial Cells

Recent studies have shown endothelial cells can be generated from hPSCs using adherent directed differentiation strategies[28, 29]. Importantly, neural cells can also be generated from pluripotent stem cells in adherent culture[30, 31]. Thus, we developed a custom 2-dimensional hPSC differentiation strategy that promotes neural and endothelial co-differentiation, in essence providing an embryonic brain-like microenvironment in vitro The strategy was initially implemented using the IMR90-4 iPS line[13], and protocol robustness subsequently validated with multiple iPSC and hESC cell lines (FIG. 2a).

Briefly, IMR90-4 iPSCs were expanded on Matrigel-coated plates in defined mTeSR1 medium[32] for 2-3 days. To initiate neural and endothelial co-differentiation, the colonies were subjected to unconditioned medium (UM, see Materials and Methods for details). After 3-4 days of UM treatment, we observed large numbers of cells expressing nestin (FIG. 2b [panel i], green), a marker of immature cells including neural progenitors, and βIII tubulin (FIG. 2b [panel i], red), a neuronal marker. When quantifying the distribution using flow cytometry, 86% of the cells could be classified as potential neural progenitors (23% nestin$^+$/βIII tubulin$^-$), immature neurons (58% nestin$^+$/βIII tubulin$^+$) or neurons (5% nestin$^-$/βIII tubulin$^+$), representing a largely embryonic brain-like microenvironment (FIG. 2c). By day 6 of UM treatment, nestin$^+$ and βIII tubulin$^+$ cells were still readily observed (FIG. 2b [panel ii]), but significantly more nestin$^-$/βIII tubulin$^+$ neurons were present (26%) while the nestin$^-$/βIII tubulin$^+$ population had decreased to 29% (FIG. 2c). Within this large immature neural population (at 3-4 days of UM treatment), very small clusters of cells having endothelial morphology and PECAM-1 expression, but lacking characteristic BBB tight junctions or glucose transporter (GLUT-1) expression, began to form (FIG. 2d [panel i], FIG. 2e, and data not shown).

Figure 2:
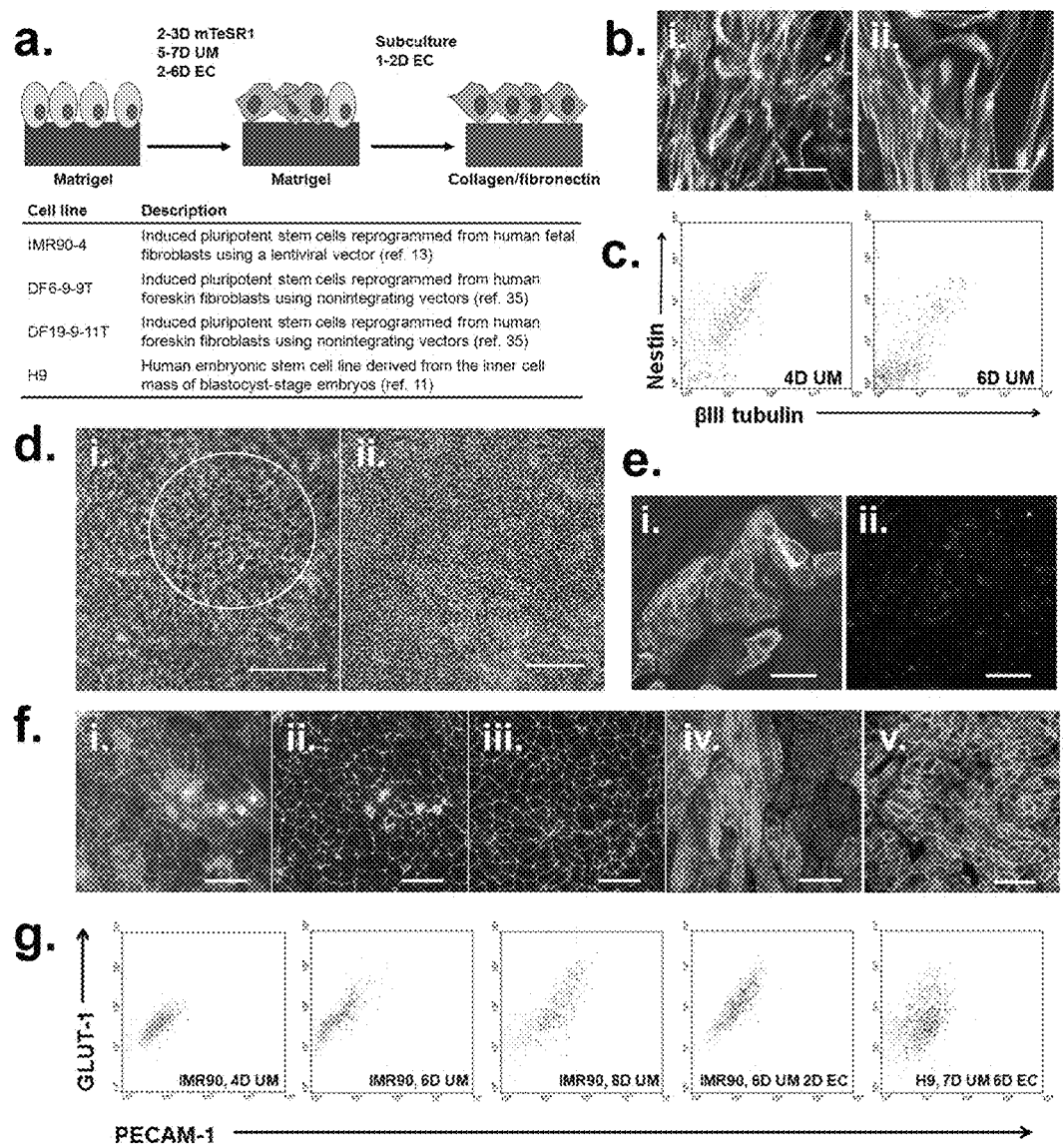
FIG. 2 shows differentiation of hPSCs to blood-brain barrier endothelial cells. (a) Schematic of BMEC differentiation protocol. hPSCs are seeded onto Matrigel in mTeSR1 medium for 2-3 days to allow adherence and colony expansion, then cultured in unconditioned medium for 5-7 days until large colonies with characteristic endothelial cell (EC) morphology are observed. Addition of defined EC medium for 2-6 days facilitates EC expansion prior to subculture onto a collagen/fibronectin matrix for further expansion and purification. iPSC and hPSC lines used in this study and their descriptions are listed. UM=unconditioned medium, EC=endothelial cell medium. (b) βIII tubulin (red) and nestin (green) expression is detected after differentiation of IMR90-4 iPSCs in UM for 4 days (panel i) and 6 days (panel ii). Scale bars indicate 50 μm. (c) Flow cytometry distributions of IMR90-4-derived βIII tubulin+ and nestin+ events at day 4 and day 6 of UM treatment. Red dots indicate βIII tubulin+/nestin+ events, blue dots indicate βIII tubulin+/nestin− events, green dots indicate βIII tubulin−/nestin+ events, and black dots indicate βIII tubulin−/nestin− events. The data are representative of two biological replicates. (d) Phase contrast image of IMR90-4 iPS cells after 3 days in UM (i) and 6 days in UM with 3 additional days in EC medium (ii). The circle in (i) indicates a small region with flattened cobblestone EC morphology and is the type of region probed with antibodies in panel 1e. This morphology is shown to be widespread in panel (ii) and corresponds to the regions identified by immunolabeling in panel 1f and FIG. 6. Scale bars indicate 200 μm. (e) IMR90-4 iPS cells cultured for 4 days UM give rise to PECAM-1+ cells (i) that do not express tight junction protein claudin-5 (ii). Scale bars indicate 50 μm. (f) After 5-7 days of UM treatment, IMR90-4-derived ECs now co-express PECAM-1 (i, red) and claudin-5 (ii, green, same field). Within these EC colonies, expression of characteristic BBB markers occludin (iii), p-glycoprotein (iv), and GLUT-1 (v) is also observed. All scale bars indicate 50 μm. (g) Flow cytometry dot plots demonstrate the temporal evolution of the GLUT-1+/PECAM-1+ population within differentiating IMR90-4 iPS or H9 hES cells. Green dots indicate PECAM-1−/GLUT-1− events, blue dots indicate PECAM-1+/GLUT-1− events, and red dots indicate PECAM-1+/GLUT-1+ events. Full quantitative results are found in Table 2.
Figure 3:
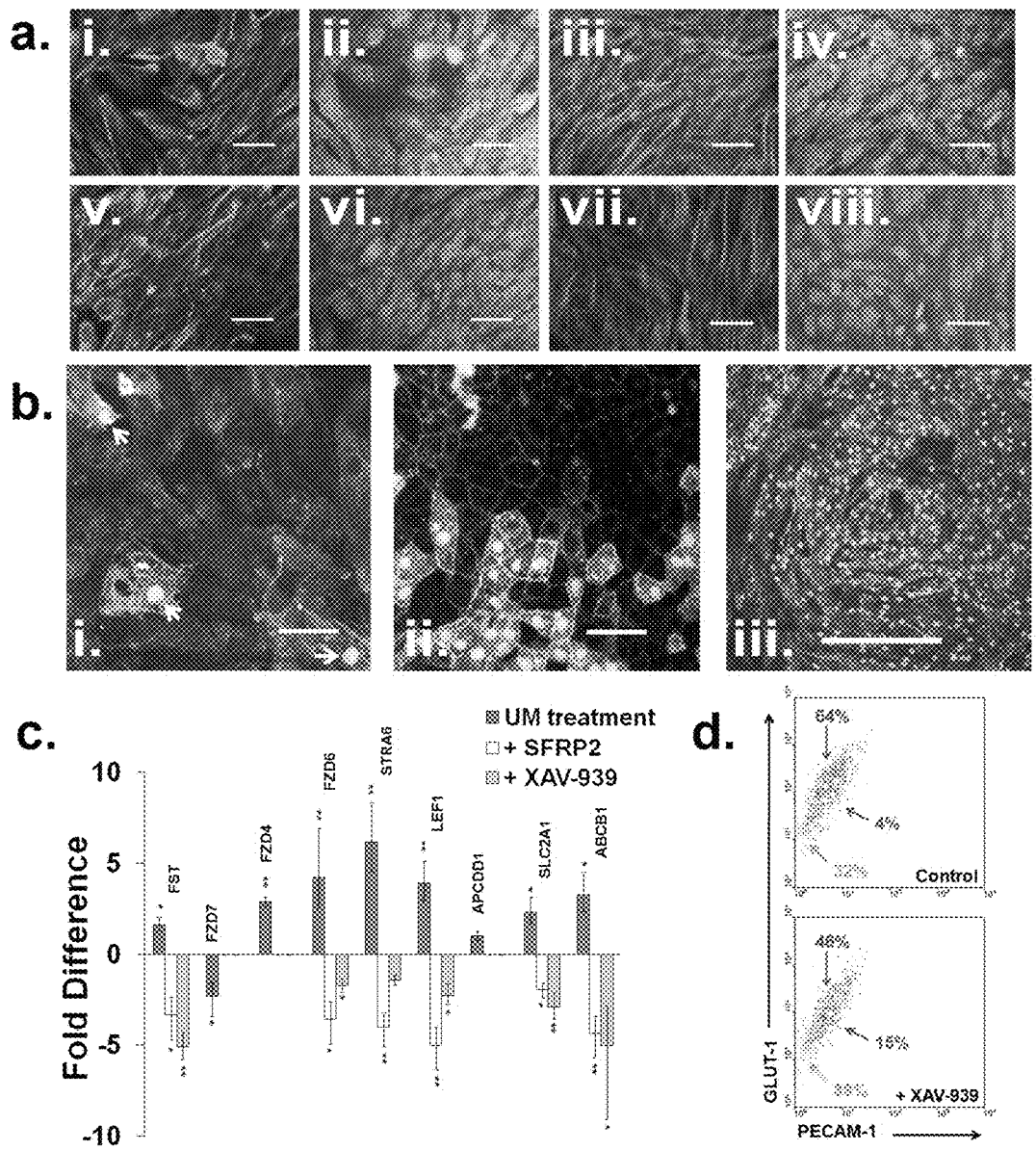
FIG. 3 shows Wnt/β-catenin signaling involvement in blood-brain barrier specification from human pluripotent stem cell-derived endothelial cells. (a) Combined fluorescence in situ hybridization/immunocytochemistry of IMR90-4 cultures at day 4 of UM treatment shows nestin+ (red; panels i and v) and βIII tubulin+ (red; panels iii and vii) cells express both WNT7A (green; panels ii and iv) and WNT7B (green; panels vi and viii). WNT7A/7B are shown overlaid with DAPI nuclear stain (blue). Panels i and ii, iii and iv, v and vi, and vii and viii are the same field. Scale bars indicate 50 μm (b) Nuclear β-catenin localization increases with differentiation time. Nuclear β-catenin (green) is sparsely observed in IMR90-4-derived PECAM-1+ (red) EC clusters after 4 days of UM treatment (panel i). Arrowheads indicate nuclear β-catenin. Nuclear β-catenin localization (green) increases after 5 days of UM treatment (panel ii) and BBB marker GLUT-1 (red) is only observed elevated in cells that also have nuclear β-catenin. After 6 days of UM and 2 days of EC medium treatment (panel iii), nuclear β-catenin (green) is co-localized with the majority of PECAM-1+ cells (red). Scale bars in panel i and panel ii indicate 50 μm and scale bar in panel iii indicates 100 μm. (c) Quantitative RT-PCR comparing fold difference gene expression in differentiating IMR90-4 iPS cells demonstrates that Wnt-activated gene expression is temporally correlated with the observed time course of BBB differentiation. The dark bars compare IMR90-4 cells treated with UM for 3 days and 7 days. A positive fold difference represents gene upregulation at 7 days of UM treatment. The white bars examine IMR90-4 cells treated with UM containing SFRP2 for 7 days. A negative fold difference represents a downregulation of gene transcription in cells treated with UM containing SFRP2 compared to cells only treated with UM. The grey bars indicate IMR90-4 cells treated with XAV-939 from days 2 thru 7 of UM treatment compared to cells treated with DMSO vehicle control. FZD4, FZD7, and APCDD1 expression were not tested in the presence of inhibitors. Error bars indicate standard deviation calculated from triplicate samples. Data are representative of two biological replicates. Statistical analysis was performed using Student's unpaired t-test; *, $p<0.05$; **, $p<0.005$. Because these cultures are heterogeneous, observed gene differences may not be exclusively ascribed to BMEC differentiation. (d) Flow cytometry of IMR90-4 cells at 6 days of UM and 2 days of EC medium treatment after addition of XAV-939 or DMSO vehicle control starting at day 2 of UM treatment. Cells treated with DMSO show similar distribution to untreated cells (64% PECAM-1+/GLUT-1+ and 68% PECAM-1+ overall; Table 2). Cells treated with XAV-939 show a small reduction in overall PECAM-1 labeling (61% total) and a marked decrease in the number of PECAM-1+/GLUT-1+ cells (46% total) (Table 2). Red dots indicate PECAM-1+/GLUT-1+ events, blue dots indicate PECAM-1+/GLUT-1− events, and green dots indicate PECAM-1−/GLUT-1− events. Data are representative of three biological replicates.

After 5-7 days of UM treatment, when the neural population was maturing, these endothelial regions became larger and more prevalent, and BBB glucose transporter GLUT-1, tight junction proteins occludin and claudin-5, and p-glycoprotein were co-expressed in the endothelial population (FIG. 2f). Although other cell types including epithelial cells and peripheral endothelia are known to express one or more of these markers, epithelial keratins K14 and K18, and the p63 transcription factor expressed in stratified epithelial cells were not detected and the composite set of markers is quite restrictive to the endothelium comprising the brain microvasculature compared with peripheral endothelia[33] (further molecular and phenotypic validation is discussed in FIGS. 3 and 4). Therefore, these cells will be referred to as hPSC-derived brain microvascular endothelial cells (hPSC-derived BMECs) throughout this application. The population of hPSC-derived BMECs was quantified by flow cytometric analysis of cells having both elevated GLUT-1 expression and PECAM-1 expression (GLUT-1$^+$/PECAM-1$^+$), and for IMR90-4-derived BMECs, this population comprised about 30% of the cultures at day 6 of UM treatment (FIG. 2g and Table 2).

TABLE 2

Quantitative assessment of hPSC-derived BMEC differentiation

| Differentiation time$^a$ | % GLUT-1$^+$/ PECAM-1$^+$ | % PECAM-1$^+$ overall | Mean per cell expression of GLUT-1$^b$ (A.U.) |
|---|---|---|---|
| IMR90-4 cell line | | | |
| 4D UM | 0 | 5 | N/A |
| 6D UM | 30 | 36 | 99 |
| 6D UM 1D EC | 36 | 42 | 221 |
| 6D UM 2D EC | 66 | 68 | 300 |
| 6D UM 2D EC (+10 μM XAV-939) | 46 | 61 | 272 |

TABLE 2-continued

Quantitative assessment of hPSC-derived BMEC differentiation

| Differentiation time[a] | % GLUT-1[+]/ PECAM-1[+] | % PECAM-1[+] overall | Mean per cell expression of GLUT-1[b] (A.U.) |
|---|---|---|---|
| 6D UM 2D EC (+DMSO control) | 64 | 68 | 285 |
| 8D UM | 39 | 61 | 263 |
| C/F[c] | 100 | 100 | 553 |
| DF19-9-11T cell line | | | |
| 6D UM 1D EC | 64 | 68 | 43 |
| 6D UM 2D EC | 75 | 75 | 70 |
| C/F[c] | 100 | 100 | 76 |
| H9 cell line | | | |
| 6D UM | 28 | 46 | 95 |
| 6D UM 2D EC | 16 | 41 | 110 |
| 7D UM 6D EC | 35 | 63 | 109 |

[a]Refers to time in unconditioned medium (UM), followed by time in EC medium (EC).
[b]Mean per cell expression of GLUT-1 in arbitrary units as measured by flow cytometry. Baseline values for GLUT-1 as described in the Materials and Methods section are different for each line tested.
[c]Refers to cells subcultured on fibronectin/collagen IV and grown to confluence.

Figure 6:
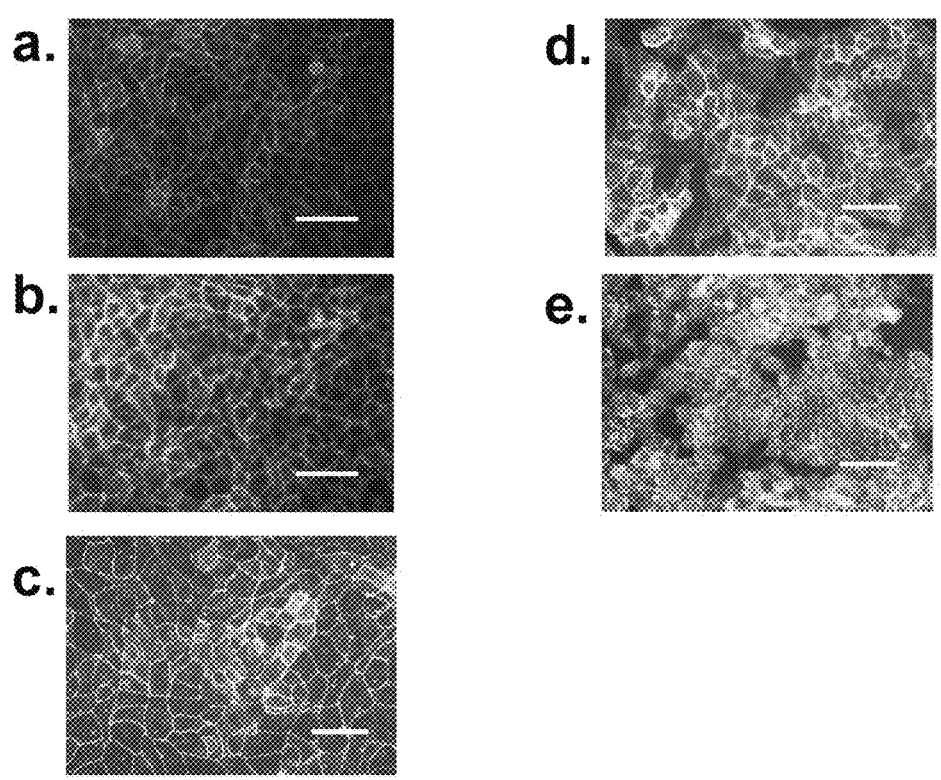
FIG. 6 shows that IMR90-4-derived BMECs express requisite BBB markers after continued differentiation in EC medium. IMR90-4-derived BMECs were cultured for 6 days in UM and 2 days in EC medium prior to immunolabeling. (a-b) PECAM-1 (a) co-expressed with claudin-5 (b). (c) PECAM-1 (red) co-expressed with occludin (green). (d) PECAM-1 (red) co-expressed with GLUT-1 (green). (e) PECAM-1 (red) co-expressed with p-glycoprotein (green). All scale bars indicate 50 µm.

This hPSC-derived BMEC population was further expanded for 2 days in a custom EC medium that included factors known to facilitate primary BMEC growth with some selectivity (basic fibroblast growth factor (bFGF) and platelet poor plasma derived serum[34], see Materials and Methods for details), and the percentage of GLUT-1[+]/PECAM1[+] cells in the differentiating IMR90-4 culture increased to 66% (FIG. 2d [panel ii], FIG. 2g, and Table 2). All GLUT-1[+]/PECAM1[+] cells also co-expressed the requisite BBB markers at this point (FIG. 6). Moreover, in the EC medium, the hPSC-derived BMEC exhibited a commensurate increase in BBB properties as indicated by substantially elevated per cell expression of GLUT-1 protein (Table 2). In contrast, if instead the cultures were grown for two additional days in UM (8 days UM) rather than in EC medium, the percentage of IMR90-4-derived BMECs increased to a lesser extent although the total PECAM-1[+] population increased to similar levels (FIG. 2g and Table 2), revealing the importance of the EC medium treatment for the selective expansion and specification of the BMEC population.

Figure 7:
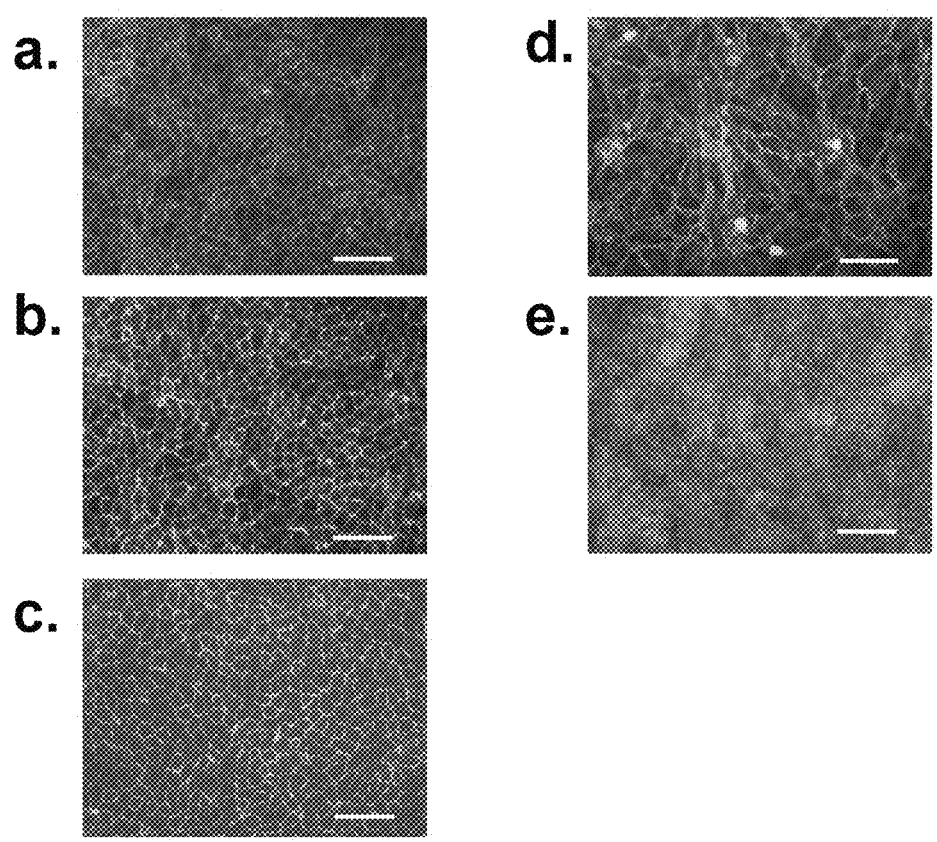
FIG. 7 shows that DF19-9-11T-derived BMECs express requisite BBB markers. DF19-9-11T-derived BMECs were cultured for 6 days in UM and 2 days in EC medium prior to immunolabeling. (a-b) PECAM-1 (a) is shown co-expressed with claudin-5 (b). (c) Expression of occludin. (d) Expression of GLUT-1. (e) Expression of p-glycoprotein. All scale bars indicate 50 µm.
Figure 8:
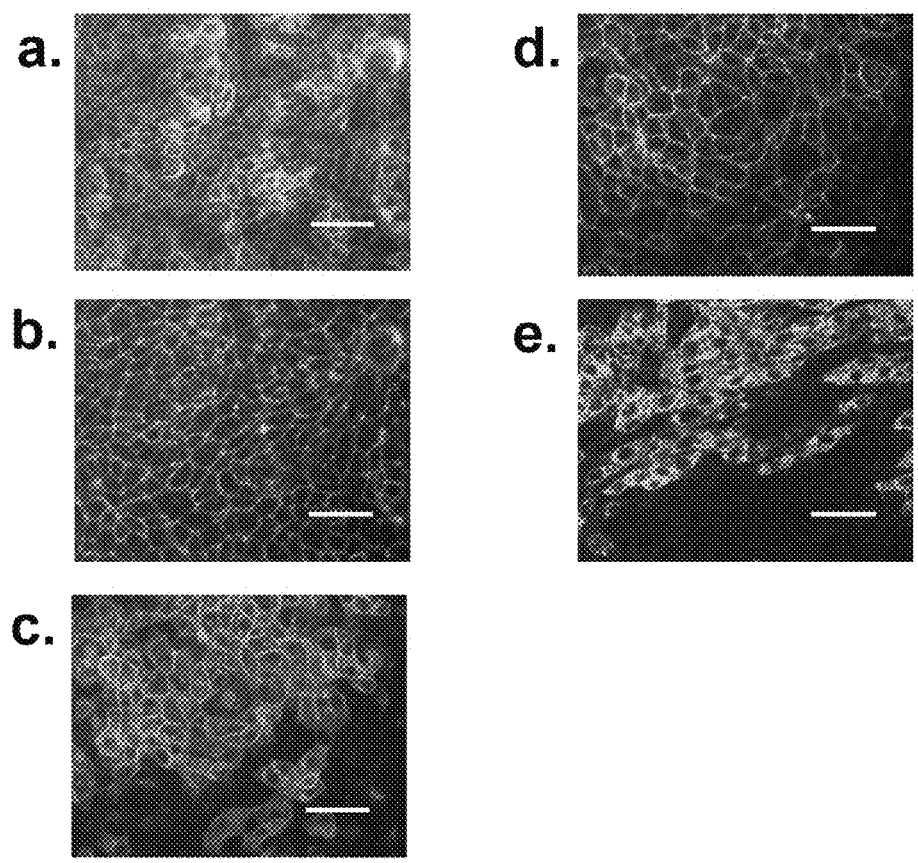
FIG. 8 shows that DF6-9-9T-derived BMECs express requisite BBB markers. DF6-9-9T-BMECs were cultured for 6 days in UM and 2 days in EC medium prior to immunolabeling. (a-b) PECAM-1 (a) is shown co-expressed with occludin (b). (c-d) GLUT-1 (c) is shown co-expressed with claudin-5 (d). (e) Expression of p-glycoprotein. All scale bars indicate 50 µm.
Figure 9:
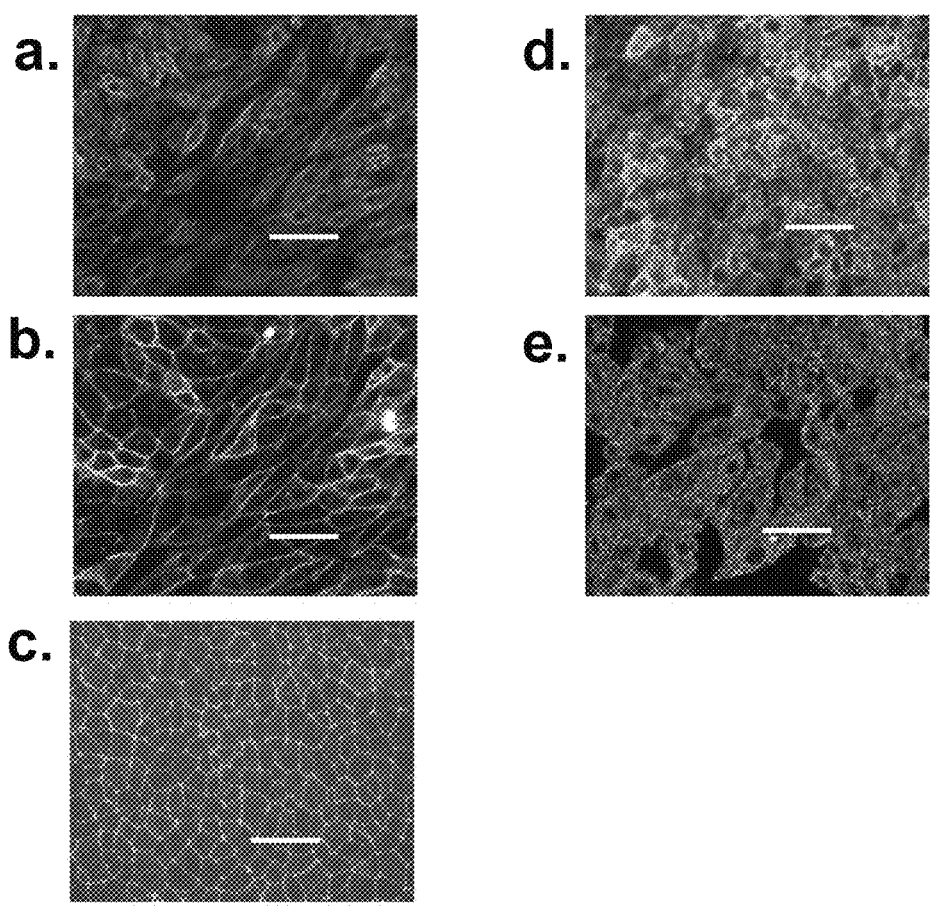
FIG. 9 shows that H9-derived BMECs express requisite BBB markers. H9-derived BMECs were cultured for 7 days in UM and 6 days in EC medium prior to immunolabeling. (a-b) PECAM-1 (a) is shown co-expressed with claudin-5 (b). (c) Expression of occludin. (d) Expression of GLUT-1. (e) Expression of p-glycoprotein. All scale bars indicate 50 µm.

Similar results were observed for the additional iPSC[35] and hESC[11] lines tested (FIG. 2a), with cell line-dependent yields and purity of BMECs (FIGS. 7-9 and Table 2). BMEC percentages from the DF19-9-11T iPSC line were 75% after 6 days UM and 2 days of EC medium treatment (Table 2). In contrast, with the H9 hESC line, extended culture (7 days UM, 6 days EC medium) was required to yield BMECs totaling 35% of the population (FIG. 2g and Table 2).

Thus, in general, 2-dimensional differentiation and expansion of hPSCs for 6-7 days in UM followed by 2-6 days in EC medium was sufficient to generate cell populations highly enriched in hPSC-derived BMECs.

Involvement of Neural Cell Co-Differentiation and Wnt/β-Catenin Signaling in the hPSC-Derived BMEC Specification Process Once we established that it was possible to derive a population of ECs possessing characteristic BMEC traits, we investigated the BMEC specification process, focusing on the potential involvement of the co-differentiating neural cells specifically through the Wnt/β-catenin pathway. Murine in vivo and in vitro studies have demonstrated that canonical Wnt/β-catenin signaling is necessary for the onset of brain angiogenesis and the acquisition of BBB properties such as GLUT-1 (refs. 26, 27) and Claudin-5 expression[36].

Canonical Wnt ligands Wnt7a and Wnt7b have been specifically implicated in BBB development in vivo, canonical Wnt ligand Wnt3a has been shown to modulate BBB properties in vitro, and several other Wnt family members are also expressed in discrete regions of the developing brain and spinal cord[26, 27, 36].

Figure 11:
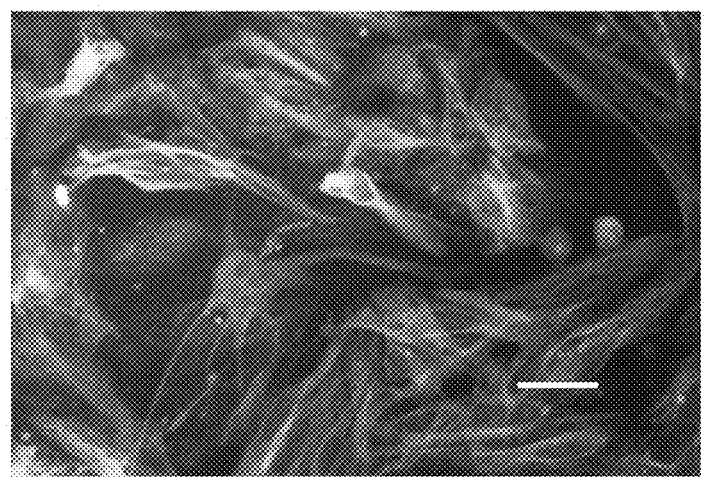
FIG. 11 shows identification of GFAP$^+$ cells in the differentiating IMR90-4 cultures. Glial fibrillary acidic protein-positive (GFAP$^+$) cells (red) could be identified among the βIII tubulin$^+$ cells (green) by immunocytochemistry at day 6 of UM treatment. Scale bars indicate 50 µm. Astrocytes were not present in significant quantities as judged by flow cytometry (data not shown).

While we had already confirmed that the majority of cells in our differentiating cultures were either neural progenitors, neurons, or ECs, we assayed for the presence of glial fibrillary acidic protein (GFAP), a marker for astrocytes, to ensure these cells were not responsible for BBB induction. At day 6 of UM treatment, small clusters of GFAP[+] (FIG. 11) cells on the order of just 30-50 cells per 10[6] could be identified by immunocytochemistry, indicating these cells were unlikely to be responsible for BMEC specification. These observations fit well into a growing body of literature that suggests the early onset of BBB properties occurs in the presence of an embryonic brain environment prior to astrocyte development[24, 26, 27, 36, 37].

Figure 12:
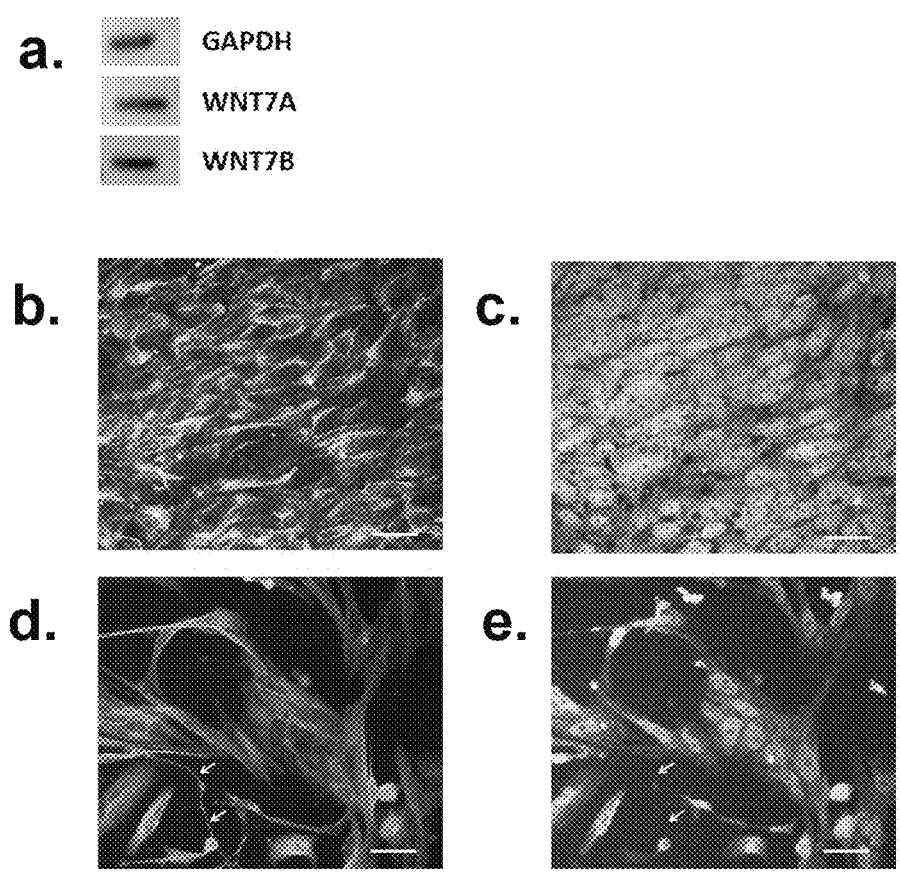
FIG. 12 shows results of examination of neural cells and Wnt signaling in the differentiating IMR90-4 iPSC cultures. (a) Expression of WNT7A and WNT7B detected by RT-PCR at 4 days of UM treatment. (b-c) Expression of nestin (b) and WNT7A (c) were detected by combined in situ hybridization/immunocytochemistry at day 6 of UM treatment. (d-e) Expression of βIII tubulin (d) and WNT7A (e) were detected at day 6 of UM treatment. Arrowheads indicate a cell with positive expression of βIII tubulin that lacks WNT7A expression. Panels (b) and (c), and panels (d) and (e), are the same field. Scale bars indicate 50 µm.
Figure 13:
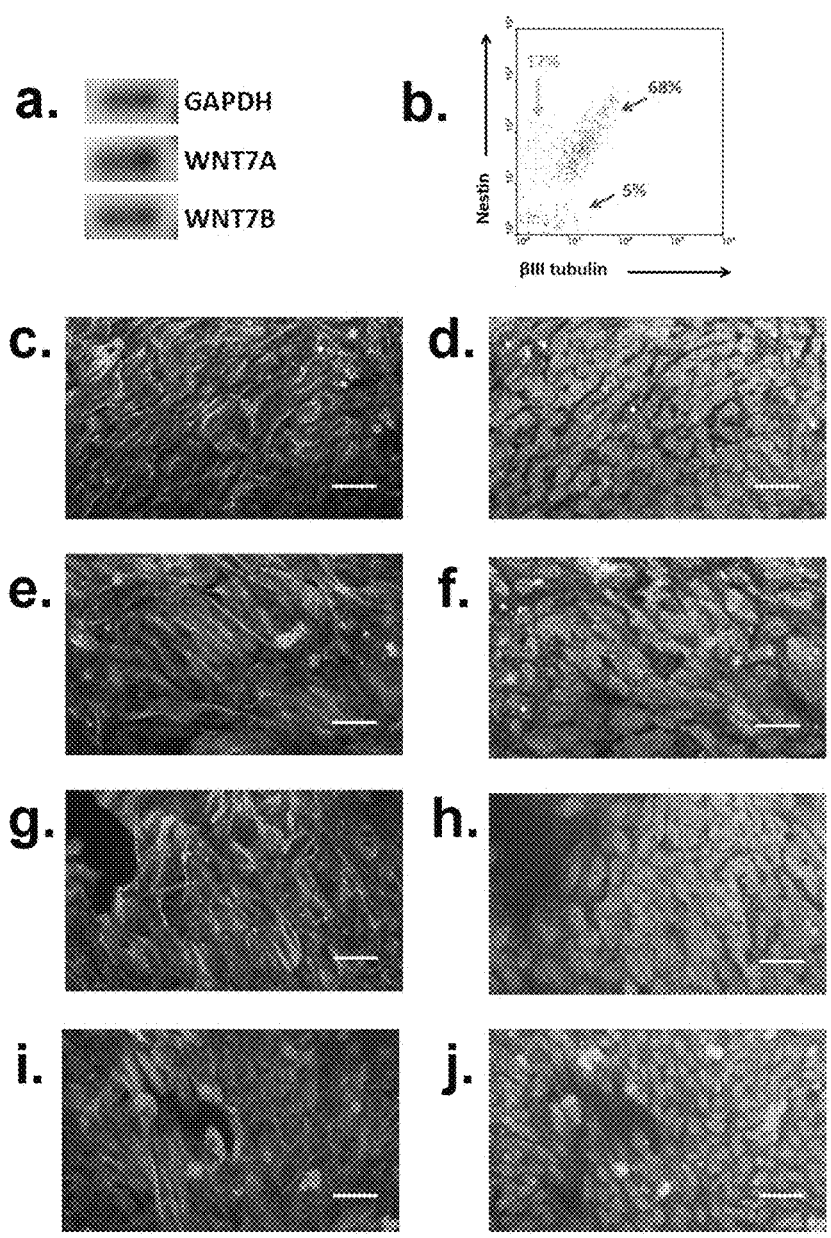
FIG. 13 shows results of examination of neural cells and Wnt signaling in the differentiating H9 hESC cultures at day 4 of UM treatment. (a) Expression of WNT7A and WNT7B detected by RT-PCR at 4 days of UM treatment. Flow cytometry distribution of differentiating H9 hESCs at day 4 of UM treatment. Green dots indicate nestin$^+$/βIII tubulin$^-$ events, red dots indicate nestin$^+$/βIII tubulin$^+$ events, blue dots indicate nestin$^-$/βIII tubulin$^+$ events, and black dots indicate nestin$^-$/βIII tubulin$^-$ events. (c-d) Expression of nestin (c) and WNT7A (d) were detected by combined in situ hybridization/immunocytochemistry. (e-f) Expression of βIII tubulin (e) and WNT7A (f). (g-h) Expression of nestin (g) and WNT7B (h). (i-j) Expression of βIII tubulin (i) and WNT7B (j). Scale bars indicate 50 µm. Adjacent horizontal panels represent the same field.

We next assayed for WNT7A and WNT7B expression in the neural progenitor/neuron populations. Analysis of the co-differentiating cultures by RT-PCR indicated that WNT7A and WNT7B transcripts were expressed at day 4 of UM treatment in IMR90-4 and H9 cultures when EC are just beginning to differentiate (FIGS. 12a and 13a). Combined immunocytochemistry and fluorescence in situ hybridization demonstrated that nearly all nestin[+] cells and βIII tubulin[+] cells (i.e. all three developing neural populations evaluated in FIG. 3c) expressed WNT7A and WNT7B transcripts at this time point (FIG. 3a). At day 6 of UM treatment for IMR90-4 cultures when large percentages of the culture had adopted a BMEC phenotype, some bipotent βIII tubulin[+] cells did not express the WNT7A transcripts, but the majority of the nestin[+] and βIII tubulin[+] cells maintained expression of WNT7A (FIG. 12b-12e), while the WNT7B transcript was no longer observed in these cells (data not shown). Differentiating H9 cultures, which possessed a distribution of neural progenitors/neurons at day 4 of UM treatment that was similar to the IMR90s (FIG. 13b), were also analyzed for WNT7A and WNT7B transcript expression and results mirrored that found for IMR90-4 cultures with both transcripts being widely expressed in nestin[+] cells and βIII tubulin[+] cells (FIG. 13c-13j).

Figure 10:
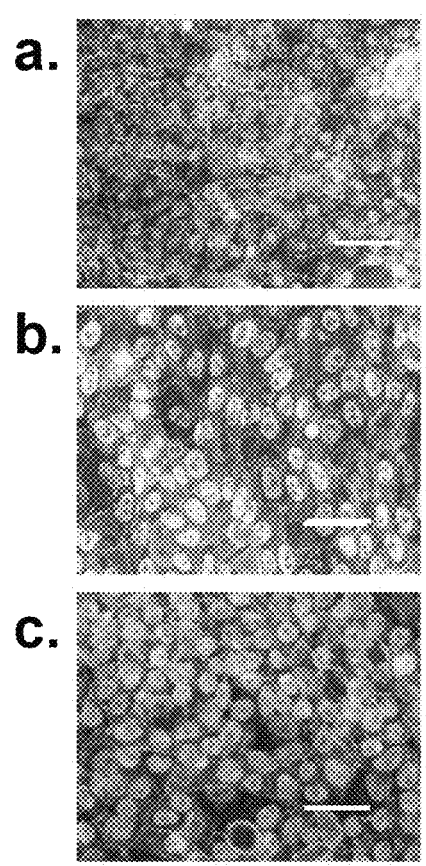
FIG. 10 shows examples of DF19-9-11T, DF6-9-9T, and H9 derived BMECs which demonstrate β-catenin nuclear localization during BMEC specification. (a) After 6 days in UM and 2 days in EC medium, DF19-9-11T-derived BMECs were immunolabeled for PECAM-1 expression (red) and β-catenin (green). (b) After 6 days in UM and 2 days in EC medium, DF6-9-9T-derived BMECs were immunolabeled for GLUT-1 (red) and β-catenin (green). (c) After 7 days in UM and 3 days in EC medium, H9-derived BMECs were immunolabeled for GLUT-1 (red) and β-catenin (green). Scale bars represent 50 µm.

Once we established WNT expression by the co-differentiating neural cells, the activation of the canonical Wnt/β-catenin pathway in the differentiating hPSC-derived BMECs was assayed. In the canonical Wnt/β-catenin pathway, Wnt ligands bind to Frizzled/LRP heterodimeric receptors stabilizing β-catenin, leading to its translocation to the nucleus where β-catenin complexes with TCF/LEF transcription factors and modulates transcription of specific Wnt target genes. Thus, the presence of nuclear β-catenin is one possible indicator of canonical Wnt pathway activation and the temporal localization of β-catenin in differentiating hPSC cultures was therefore monitored (FIG. 3b). While junctional β-catenin was widespread at 3-4 days of UM treatment of the IMR90-4 iPSC line, nuclear localization of β-catenin in PECAM-1[+] ECs was only sparsely observed (7±4% of total cells; FIG. 3b [panel i]). The percentage of ECs exhibiting detectable nuclear β-catenin substantially increased to 40±6% at 5 days of UM treatment (FIG. 3b [panel ii]) and nearly all PECAM-1[+] ECs (90±6%) possessed nuclear β-catenin after 6 days UM and 2 days EC treatment (FIG. 3a [panel iii]). Of note, elevated expression of the BBB membrane transport protein GLUT-1 was nearly exclusively detected in cells that also contained nuclear β-catenin (FIG. 3b [panel ii]), which correlates with in vivo reports of an absence of BBB GLUT-1 in endothelial-specific β-catenin knockout mutants[26] and GLUT-1 downregulation in the vascular plexus of WNT7A/7B double knockout mutants[27]. Differentiating DF19-9-11T and DF6-9-9T iPSC-derived ECs also exhibited nuclear β-catenin localization after 6 days UM and 2 days EC medium treatment (FIGS. 10a and 10b). The H9 hESC line demonstrated a similar progression in nuclear β-catenin localization during differentiation to BMECs, but with an extended temporal evolution and consistent with the longer times required to generate BMECs from this line; complete nuclear localization was observed after 7 days of UM and 3 days of EC medium treatment (FIG. 10c).

Given that all cell lines tested exhibited nuclear β-catenin localization, linkage of this localization to Wnt-mediated processes was also assessed by evaluating transcript expression of Wnt receptors and target genes during IMR90-4 differentiation (FIG. 3c). Gene expression levels in later (7D UM) cultures having ~30% GLUT-1+/PECAM-1+ BMECs and early (3D UM) cultures devoid of these cells were compared using quantitative RT-PCR. As expected, transcripts indicative of BMEC differentiation, ABCB1 (p-glycoprotein) and SLC2A1 (GLUT-1), were upregulated during this time period (FIG. 3c). Wnt receptors Frizzled4 (FZD4) and Frizzled6 (FZD6) have been implicated in angiogenesis of retinal[38-40] and brain ECs[26], with the FZD6 transcript being highly expressed in adult brain ECs compared with lung and liver ECs[26]. Transcripts of Frizzled4 and Frizzled6 were upregulated in concert with the emergence of IMR90-4-derived GLUT-1+/PECAM1+ BMECs in the differentiating cultures, whereas the FZD7 gene, which encodes Wnt receptor Frizzled7 that has no known linkage to brain endothelial differentiation[26, 27], was downregulated during this same time frame. The gene products for β-catenin associated transcription factor LEF1 and Wnt-downstream gene FST (encoding for follistatin) were also upregulated during this time frame. In addition, the STRA6 gene, which encodes a BBB-resident vitamin A transporter[41, 42] that has been identified as a Wnt target gene[43] and is enriched in adult brain ECs compared to lung and liver ECs[26], was upregulated during the course of BBB differentiation. APCDD1 has been noted to be highly enriched in adult brain ECs compared to lung and liver ECs[26] and was recently shown to be an antagonist of Wnt signaling[44]. While the APCDD1 transcript was expressed during BBB differentiation, it remained unchanged over the time course of analysis. Combined with the aforementioned findings[26, 44], this may suggest a more prominent APCDD1 role in adult BBB maintenance through Wnt pathway regulation rather than in BBB development.

To further demonstrate that Wnt ligands may play a key role in BMEC specification from hPSCs, we employed both secreted Frizzled Receptor Protein 2 (SFRP2), which binds to soluble Wnts and prevents upstream activation of the Wnt pathway[45], and XAV-939, a cell-permeable small molecule that inhibits Wnt signaling downstream by inhibiting tankyrase 1 and 2, thereby stabilizing axin and increasing β-catenin degradation[46]. Quantitative RT-PCR analysis of genes elevated during BMEC specification following these treatments yielded statistically significant downregulation of Wnt pathway components LEF1 and FST, BBB-relevant Wnt targets STRA6 and FZD6, and BMEC indicators SLC2A1 and ABCB1 (FIG. 3c), suggesting an effect of Wnt/β-catenin pathway inhibition on BMEC formation. Furthermore, differentiating IMR90-4 cultures treated with XAV-939 exhibited a reduction in GLUT-1+ cells from 64% to 46% (FIG. 3d and Table 2). Treatment with XAV-939 also led to a slight reduction in the overall number of PECAM-1+ cells (68% to 61%), thus giving a 20% net reduction in the overall number of PECAM-1+/GLUT-1+ BMECs. Interestingly, the presence of XAV-939 did not alter claudin-5 or occludin localization and western blots indicated equal amounts of claudin-5 and occludin in the differentiating cultures regardless of XAV-939 treatment (data not shown). These data compare favorably with observations in endothelial-specific β-catenin knockout mouse mutants where vascular malformations lacked GLUT-1 expression but still possessed tight junctions[26].

In summary, a co-differentiating neural microenvironment expressing WNT7A and WNT7B appears to impact hPSC-derived BMEC specification through the canonical Wnt/β-catenin pathway, suggesting a specification process similar to that observed in vivo[26, 27, 36]. However, as indicated by Wnt signaling inhibition with XAV-939, while certain aspects of BMEC specification appear to be influenced by the Wnt-β-catenin pathway (e.g. GLUT-1 expression), this pathway is likely not exclusively responsible for BMEC specification[47-49].

Purification of hPSC-Derived BMECs

Although the 2-dimensional co-differentiation strategy resulted in large numbers of hPSC-derived BMECs as defined by expression of tight junction proteins, p-glycoprotein, and elevated GLUT-1, many characteristic BBB properties, including barrier formation, are best evaluated in purified, confluent monolayers. Furthermore, gel electrophoresis of RT-PCR products indicated that the IMR90-4-derived BMECs, while expressing the PECAM1 transcript, lacked expression of transcripts encoding for von Willebrand factor (vWF) and VE-cadherin during the early UM treatment phase (FIG. 4a). During EC medium treatment, VE-cadherin expression was detected (FIG. 4a), consistent with sequential expression of PECAM-1 and VE-cadherin endothelial genes previously observed during EC differentiation of stem cells[50] (See Table 4 below for features of ECs). Thus, to stimulate further maturation and facilitate purification, IMR90-4-derived BMECs were subcultured from Matrigel onto plates coated with collagen/fibronectin extracellular matrix commonly used for primary BMEC culture.

TABLE 4

Features of cultured endothelial cells

| Characteristic | General endothelium | hPSC-derived BBB endothelium |
|---|---|---|
| Cobblestone morphology with contact-inhibited growth | Yes | Yes |
| Ability to form vascular tubes after VEGF stimulation in Matrigel | Yes | Yes |
| Uptake of acetylated low-density lipoprotein | Yes | Yes |
| Expression of PECAM-1 | Yes | Yes |
| Expression of von Willebrand Factor | Yes | Yes |
| Expression of VE-cadherin | Yes | Yes |

Figure 14:
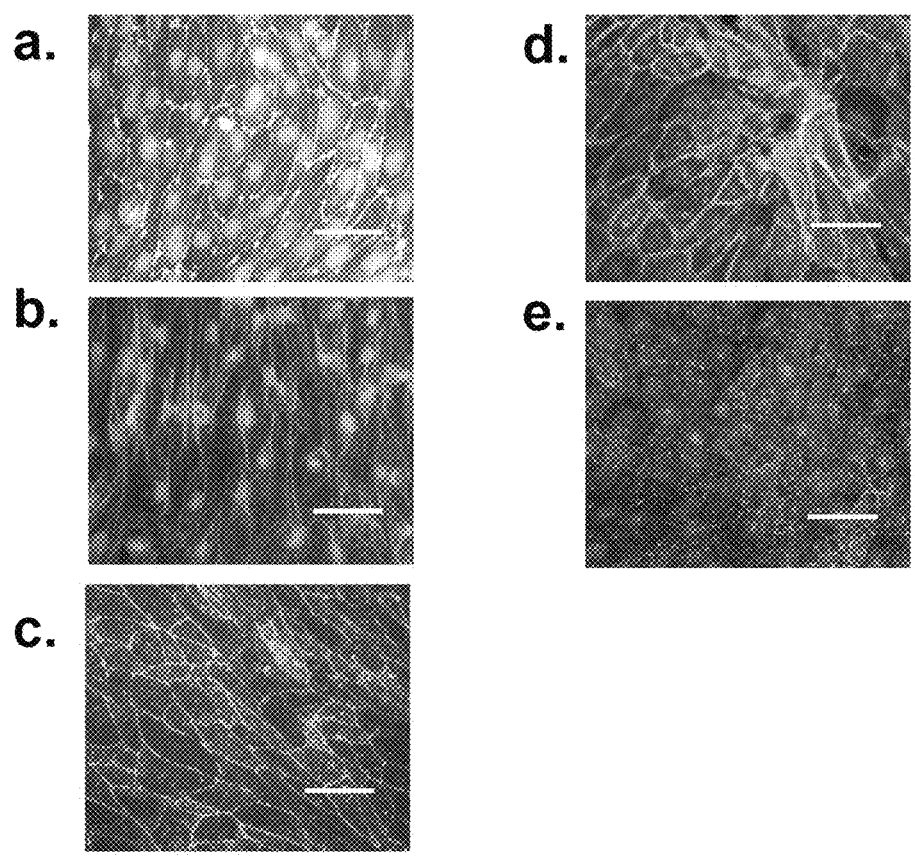
FIG. 14 shows that DF19-9-11-derived BMECs subcultured onto collagen/fibronectin-coated surface maintain BBB markers. (a) vWF (red) is shown co-localized with occludin (green) by immunofluorescence. DAPI (blue) is overlaid (b) Expression of PECAM-1 (red) overlaid with DAPI (blue). (c) Expression of claudin-5. (d) Expression of GLUT-1. (e) Expression of p-glycoprotein. All scale bars indicate 50 µm.

In EC medium, the cells grew to confluence after 1-2 days, were contact-inhibited, exhibited characteristic EC morphology (FIG. 4b), and were capable of acetylated low-density lipoprotein uptake (FIG. 4c). Approximately 100% of the cells in the cultures expressed the requisite BBB markers, indicating effective and facile purification using this extracellular matrix-based selective passaging method (FIGS. 4d and 4e). Importantly, the cells also acquired vWF and VE-cadherin expression during subculture, as demonstrated both by RT-PCR and immunocytochemistry, indicating further EC maturation (FIGS. 4a and 4e). To further confirm the endothelial phenotype of the purified BMECs, the IMR90-4-derived BMECs formed vascular tubes when dissociated and re-plated onto Matrigel for 12 hours in the presence of vascular endothelial growth factor (VEGF) (FIG. 4f). Similar purification results were found for DF19-9-11T-derived BMECs when subcultured onto the collagen/fibronectin matrix (FIG. 14 and Table 2).

Figure 15:
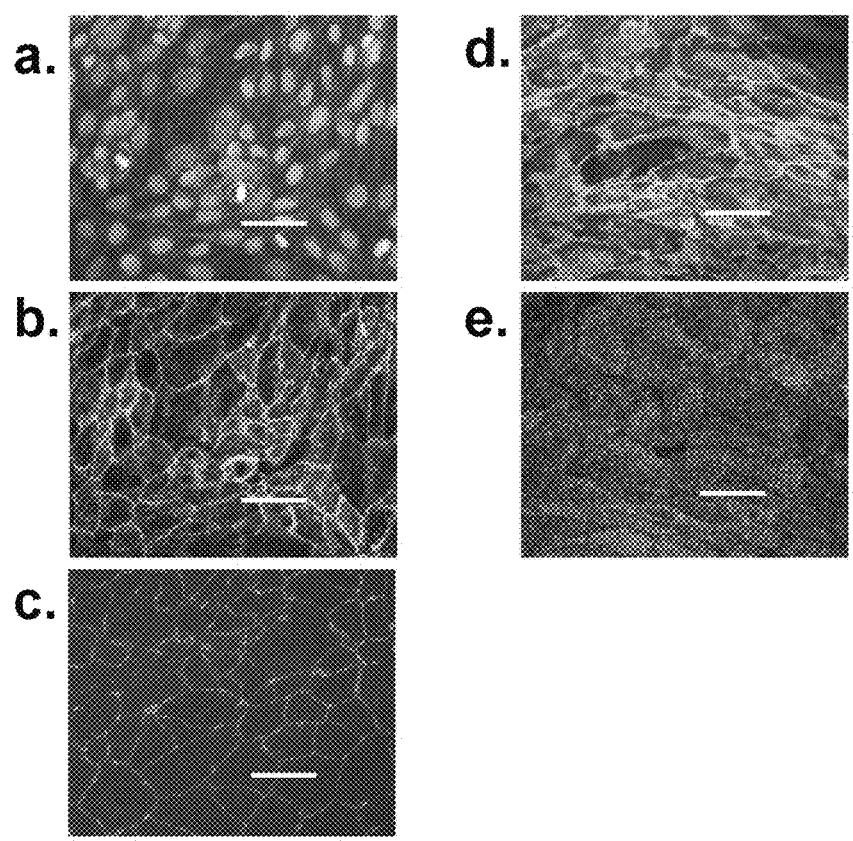
FIG. 15 shows that DF6-9-9-derived BMECs subcultured onto collagen/fibronectin-coated surfaces maintain BBB markers. (a-b) PECAM-1 (a) is shown co-expressed with claudin-5 by immunofluorescence (b). DAPI (blue) is shown overlaid with PECAM-1. (c) Expression of occludin. (d) Expression of GLUT-1. (e) Expression of p-glycoprotein. All scale bars indicate 50 µm.

The extent of maturation achieved during UM and EC medium treatment prior to subculture onto the fibronectin/collagen matrix was critical for obtaining a pure, confluent monolayer of BMECs. For example, when IMR90-4-derived BMECs were subcultured after just 4 days of UM treatment, BBB-like cells still developed, but did not reach confluence and in many areas showed malformed and discontinuous tight junctions (FIG. 4g). This lack of BBB differentiation correlated well with the observation that at this stage of UM treatment, minimal β-catenin nuclear localization (FIG. 3b) can be found and no PECAM-1$^+$/claudin-5$^+$ cells are present (FIG. 1e). Along these lines, while DF-6-9-9T-derived BMECs (FIG. 15) could be purified using the collagen/fibronectin passaging protocol developed for the IMR90-4 and DF19-9-11T lines, there was some loss of tight junction continuity (e.g. FIG. 4g). H9-derived BMECs could not be purified by the collagen/fibronectin protocol due to the presence of PECAM-1$^+$/GLUT-1$^-$ non-BBB ECs in the differentiating culture, which would also adhere to the matrix proteins. However, optimization of the expansion and passaging parameters for these lines was not pursued since the IMR90-4 and DF19-9-11T lines could already be used directly for more in-depth BBB phenotype testing as described below.

Taken together, the outlined 2-dimensional differentiation approach combined with selective purification can yield pure hPSC-derived BMEC populations expressing the requisite EC and BBB markers.

BBB Phenotype of iPSC-Derived BMECs

Figure 5:
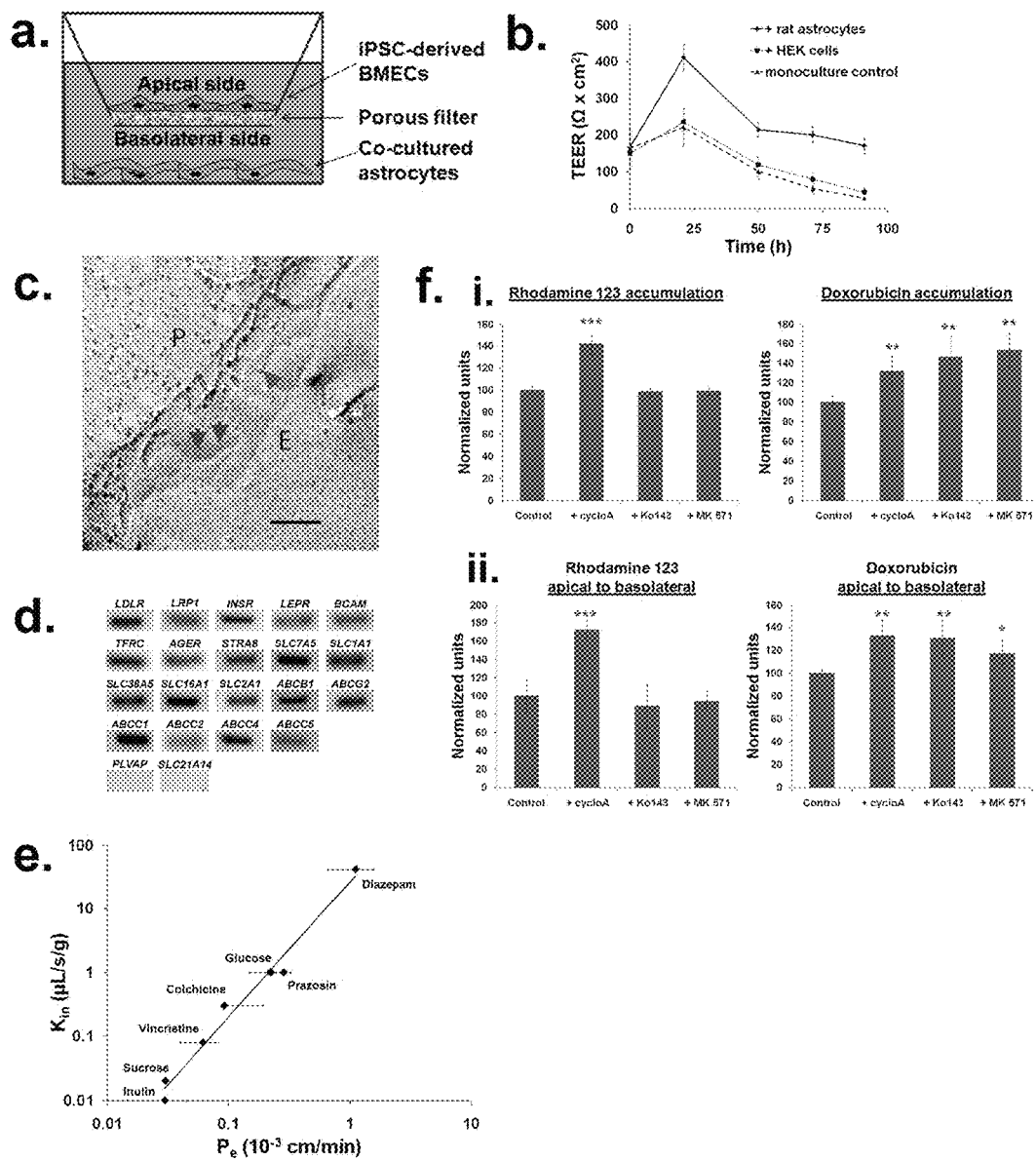
FIG. 5 shows functional barrier properties and BBB characteristics of purified iPSC-derived BMECs. (a) Schematic of a two-compartment blood-brain barrier model. iPSC-derived BMECs are seeded onto a TRANSWELL™ filter coated with collagen/fibronectin and co-cultured with rat astrocytes to assay for induction of BBB properties. Apical (blood side) and basolateral (brain side) chambers are denoted with respect to the p-glycoprotein transport assays. (b) iPSC-derived BMECs respond to soluble cues from astrocytes. IMR90-4-derived BMECs were cultured alone (monoculture) or co-cultured with either rat astrocytes or human embryonic kidney (HEK) cells for 96 hours and trans-endothelial electrical resistance (TEER) was monitored. Error bars represent standard deviation of triplicate filters from a single experiment The preferential TEER response due to astrocyte co-culture compared to HEK co-culture was observed for more than ten biological replicates. See Table 2 for TEER values from experiments with optimized medium and seeding density. (c) Freeze-fracture electron microscopy of IMR90-4-derived BMECs after co-culture with rat astrocytes for 24 hours. "P" indicates protoplasmic face (P-face) and "E" indicates endoplasmic face (E-face). Red arrowheads indicate an E-face groove absent tight junction particles, while the green arrowhead highlights a rare tight junction particle found at the E-face and the yellow arrowheads indicate the high density of tight junction particles associated with the P-face. Scale bar indicates 0.2 μm. (d) RT-PCR detection of representative blood-brain barrier transcript expression in IMR90-4-derived BMECs co-cultured with rat astrocytes. Transcript presence was confirmed for LDLR, LRP1, INSR, LEPR, BCAM, TFRC, AGER, STRA6, SLC7A5, SLC1A1, SLC38A5, SLC16A1, SLC2A1, ABCB1, ABCG2, ABCC1, ABCC2, ABCC4, and ABCC5. PLVAP and SLC21A14 transcripts were not detected. Monocultured IMR90-4-derived BMECs had a similar transcript profile except LRP1 and ABCC5 were absent, requiring co-culture with either HEK293 cells or astrocytes for their induction. (e) Correlation between IMR90-4-derived BMEC permeability coefficients ($P_e$, x-axis) and rodent in vivo transfer coefficients ($K_{in}$, y-axis). $P_e$ values (cm/min) were calculated from flux experiments using triplicate filters as described in the Material and Methods section. Each compound was measured two or three times across five different biological samples and error bars represent standard deviation calculated between biological replicates. $K_{in}$ values (µL s$^{-1}$ g$^{-1}$) were extracted from plotted in situ rodent brain perfusion data reported in Perriere et al[57]. Colchicine was the only compound with large variability across biological replicates (see Table 6 for full details). (f) Functional expression of efflux transporters in IMR90-4-derived BMECs. Accumulation of rhodamine 123 or doxorubicin was measured in the presence and absence of cyclosporin A, Ko143, or MK 571 (panel i). Transport of rhodamine 123 or doxorubicin from the apical to basolateral chambers was measured in the two compartment model in the presence and absence of cyclosporin A, Ko143, or MK 571 (panel ii). Error bars indicate standard deviation calculated from triplicate wells or filters. Data is representative of two biological replicates for each inhibition assay. Statistical significance was calculated by the Student's unpaired t-test; *, p<0.01; , p<0.05; *, p<0.1.
Figure 16:
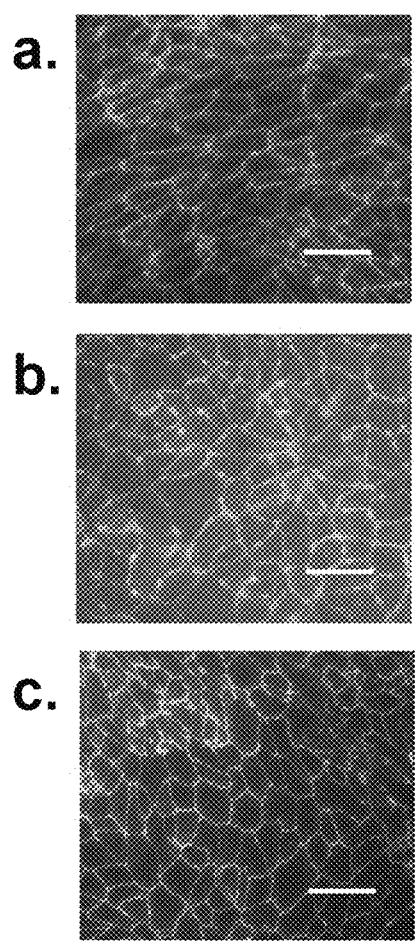
FIG. 16 shows that continuous tight junction expression is maintained by IMR90-4-derived BMECs after subculture onto collagen/fibronectin-coated TRANSWELL™ filters. (a) Expression of claudin-5 by immunofluorescence. (b) Expression of occludin. (c) Expression of ZO-1. All scale bars indicate 50 µm.

In addition to requisite BBB marker expression and vascular phenotype, iPSC-derived BMECs should also respond to astrocyte cues, exhibit tight barrier properties, and express functional transport systems. A hallmark of the BBB is the high trans-endothelial electrical resistance (TEER) that is a consequence of tight junction protein interactions between adjacent BMECs. To measure the TEER for the BMEC monolayers, IMR90-4-derived BMECs were seeded onto TRANSWELL™ filters coated with collagen/fibronectin matrix and grown to confluence in EC medium to create a standard two-compartment BBB model (FIG. 5a). Immunofluorescent detection of ZO-1, occludin, and claudin-5 demonstrated the maintenance of continuous cell-cell contacts between BMECs on the filter surface, similar to the tight junctions observed on fibronectin/collagen-coated polystyrene culture dishes (FIG. 16). Initial TEER measurements taken at confluence were 150-175 $\Omega \times cm^2$, indicative of a tightening endothelial monolayer (FIG. 5b, time 0 h). TEER measurements following co-culture with either primary rat astrocytes or non-neural human embryonic kidney (HEK) 293 cells were compared to monocultured IMR90-4-derived BMECs. After 24 hours, TEER in the astrocyte co-cultures (412±38 $\Omega \times cm^2$) nearly doubled that observed in both HEK cell co-culture (236±23 $\Omega \times cm^2$) and BMEC monoculture (222±51 $\Omega \times cm^2$), indicating a specific response to astrocyte cues as expected of BMECs (FIG. 5b and Table 3). Moreover, the astrocyte co-culture maintained elevated TEER throughout the 96 hour experiment as had been observed previously with highly pure primary rat BMECs[37], further demonstrating the ability of hPSC-derived BMECs to respond to astrocyte-specific factors.

TABLE 3

Evaluation of iPSC-derived BMEC TEER

| Co-cultured cell | Co-culture medium$^a$ | Maximum TEER ($\Omega \times cm^2$)$^b$ |
| --- | --- | --- |
| IMR90-4-derived BMECs | | |
| Monoculture | 1% PDS | 222 ± 51 |
| HEKs | 1% PDS | 236 ± 23 |
| HEKs | 10% FBS | 364 ± 53 |
| HEKs (optimized)$^c$ | 10% FBS | 899 ± 132 |
| Astrocytes | 1% PDS | 412 ± 38 |
| Astrocytes | 10% FBS | 696 ± 8 |
| Astrocytes (optimized)$^{c, d}$ | 10% FBS | 1450 ± 140 |
| DF19-9-11T-derived BMECs | | |
| Astrocytes (optimized)$^c$ | 10% FBS | 777 ± 112 |

$^a$Refers to serum component of culture media. Full media details found in Materials and Methods.
$^b$Measured at approximately 24 hours of co-culture. TEER is expressed as mean ± standard deviation measured from triplicate filters.
$^c$Refers to optimized BMEC subculture density to reduce nonspecific cell adherence and debris accumulation.
$^d$The TEER observed for this co-culture condition was typically between 700-1100 $\Omega \times cm^2$ over the course of thirty experiments.

While EC medium is effective at expanding the hPSC-derived BMEC population, it did not induce extremely tight barrier properties as evidenced by absolute TEER measurements in the 200-400 $\Omega \times cm^2$ range. If astrocyte co-culture was performed in medium containing 10% FBS, TEER in the IMR90-4-derived monolayer reached 696±8 $\Omega \times cm^2$ after 24 hours, while TEER in the HEK cell co-cultures was again significantly lower at 364±53 $\Omega \times cm^2$ (Table 3). Further optimization of TRANSWELL™ filter seeding density to generate a more uniform monolayer yielded IMR90-4-derived BMECs that achieved high TEER values of 899±132 $\Omega \times cm^2$ even with non-inductive HEK cells as the co-cultured cell type, which further confirms the acquisition of BBB properties prior to subculture. Under these same optimized conditions, maximum TEER achieved was 1450±140 $\Omega \times cm^2$ upon astrocyte co-culture (Table 3). In the presence of astrocyte co-culture, DF19-9-11T-derived BMECs exhibited a maximum TEER of 777±112 $\Omega \times cm^2$ (Table 3).

In terms of robustness, starting with iPS cells of differing passage number and utilizing different primary astrocyte isolations (with cells from fresh or frozen stocks), the co-culture model was consistently in the 700-1100 $\Omega \times cm^2$ range over the course of thirty individual experiments. For comparison, one of the highest documented TEER values for primary human BMECs obtained from fresh biopsy is 339±107 $\Omega \times cm^2$ (ref. 51) and the immortalized human BMEC cell line, hCMEC/D3, reaches a maximum TEER of 199±5 $\Omega \times cm^2$ in response to hydrocortisone[9]. To further validate the fidelity of the tight junctions formed by the IMR90-4-derived BMECs after co-culture with astrocytes, these cells were subjected to freeze-fracture electron microscopy (FIG. 5c). Freeze-fracture revealed complex networks of tight junction strands that were primarily associated with the protoplasmic fracture face (P-face) similar to that of high resistance BBB endothelium in vivo[52].

The BBB in vivo is not only characterized by its high TEER, but also by its impermeability to passive diffusion, expression of various transport systems used for import and export of nutrients and metabolites, and its ability to act as an active barrier to small hydrophobic molecules by employing key efflux transporters like p-glycoprotein, breast cancer resistance protein (BCRP), and members of the multidrug resistance protein (MRP) family[53]. Purified IMR90-4-derived BMECs in the astrocyte co-culture system expressed transcripts encoding a variety of receptors/transporters found at the BBB (FIG. 5d), such as LDLR (low density lipoprotein receptor), LRP1 (low density lipoprotein receptor-related protein 1), INSR (insulin receptor), LEPR (leptin receptor), BCAM (lutheran glycoprotein), TFRC (transferrin receptor), and AGER (receptor for advanced glycation endproducts, RAGE). Transcript was also detected for members of amino acid and peptide transporter families that are highly enriched at the BBB compared to other endothelium, including STRA6 (retinol binding protein), SLC2A1 (GLUT-1), SLC7A5 (LAT1), SLC1A1 (EAAT3), SLC38A5 (SNAT5), and SLC16A1 (MCT1). Efflux transporter transcripts were also detected, including ABCB1 (MDR1/p-glycoprotein), ABCG2 (BCRP), ABCC1 (MRP1), ABCC2 (MRP2), ABCC4 (MRP4), and ABCC5 (MRP5).

Of note, two assayed transcripts were not detected: PLVAP and SLC21A14. PLVAP (plasmalemma vesicle-associated protein) is initially expressed at the BBB during development and becomes downregulated with onset of barrier properties while its expression remains in peripheral vessels throughout adulthood[24]. Thus, the absence of PLVAP in the hPSC-derived BMECs is a further indicator of BBB specification and maturation. SLC21A14 (also known as SLCO1C1) encodes Oatp14, an organic anion transporter whose transcript is highly enriched at the rodent but not human BBB[54]; Oatp14 was also found to be under the limit of quantitative detection in a recent BBB proteomics study of human brain microvasculature[55], and its absence in the human iPSC-derived BMECs suggests the possibility of species-dependent properties. Taken together, the gene expression profile of receptors and transporters is highly representative of a BBB endothelial cell.

To demonstrate the exclusionary barrier properties of the iPSC-derived BMEC/astrocyte co-culture model, the permeability of a BBB-impermeant small molecule tracer (sodium fluorescein; 376 Da) was first assessed. The fluorescein permeability coefficient ($P_e$) for IMR90-4-derived BMECs was measured to be $2.2\pm0.1\times10^{-6}$ cm/min and DF19-9-11T-derived BMECs provided an average $P_e$ of $5.1\pm0.9\times10^{-6}$ cm/min. By comparison, reported sodium fluorescein $P_e$ values for the hCMEC/D3 line and primary human BMECs were $3.4\times10^{-3}$ (ref. 9) and $3.2\times10^{-3}$ (ref. 56) cm/min, respectively, which are roughly 1000-fold more permeable than the iPSC-derived systems. Next, radiolabeled small molecules with varying sizes, lipophilicity, and efflux transporter recognition were screened for relative permeability using the IMR90-4-derived BMEC/astrocyte co-culture model (FIG. 5e and Table 5). The measured $P_e$ values showed very good correlation ($R^2=0.98$) to in vivo brain uptake in rodents measured by in situ brain perfusion. Sucrose, a small (342 Da), hydrophilic molecule with limited BBB uptake, was found to have a $P_e$ value of $3.04\times10^{-5}$ cm/min, while glucose, a small (180 Da), hydrophilic molecule that is actively transported across the BBB by the GLUT-1 transporter, demonstrated 7-fold higher permeation ($P_e=2.22\times10^{-4}$ cm/min). Diazepam, a very lipophilic small molecule that demonstrates high BBB penetration in vivo because it is not an efflux transporter substrate, also showed the highest in vitro permeation ($1.11\times10^{-3}$ cm/min). Colchicine and vincristine, which are also lipophilic small molecules that have limited brain uptake in vivo since they are substrates of p-glycoprotein and MRP family members (Table 5), were accordingly found to have lower $P_e$ values in vitro ($9.19\times10^{-5}$ and $6.18\times10^{-5}$ cm/min, respectively). Prazosin, which is effluxed by BCRP but also thought be to be influxed by an organic cation transporter (Table 5), showed slightly higher $P_e$ ($2.86\times10^{-4}$ cm/min) than colchicine and vincristine, correlating to its in vivo ranking. Importantly, the 40-fold dynamic range of $P_e$ values (diazepam/insulin/sucrose) was much larger than in previously reported human models (hCMEC/D3=2-10-fold difference[8]), and along with the high $P_e$ correlation to in vivo data suggests the suitability of the iPSC-derived BBB model as a drug screening tool.

TABLE 5

In vitro permeability of the IMR90-4-derived BMECs.

| Compound | Molecular Weight (g/mol) | Octanol/water partition coefficient (logD)[1-6] | Transporter recognition[7-10] | Average Pe ($10^{-3}$ cm/min)[b] |
|---|---|---|---|---|
| Inulin | Variable[a] | −0.25 | None | 0.029 ± 0.015 |
| Sucrose | 342 | −3.3 | None | 0.03 ± 0.0016 |
| Glucose | 180 | −2.8 | GLUT-1 (influx) | 0.22 ± 0.07 |
| Vincristine | 825 | 2.8 | MDR1, MRP1, MRP2 | 0.06 ± 0.02 |
| Colchicine | 399 | 1.03 | MDR1, MRP1 BCRP (efflux), | 0.09 ± 0.1 |
| Prazosin | 383 | 2.16 | Organic cation transporters (influx) | 0.29 ± 0.04 |
| Diazepam | 285 | 2.82 | None | 1.11 ± 0.45 |

[a]Inulin is a polysaccharide polymer with an unspecified chain length.
[b]Mean ± standard deviation was calculated from three biological replicates except sucrose (two replicates).

Figure 17:
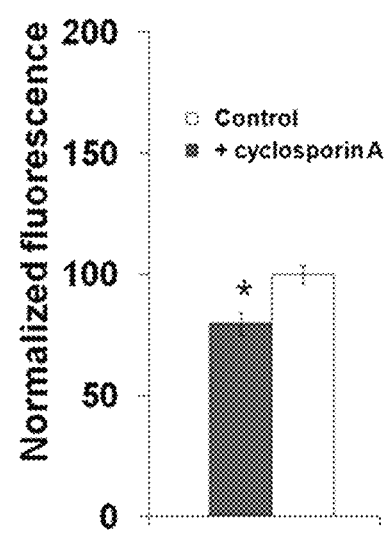
FIG. 17 shows that basolateral to apical transport of rhodamine 123 decreases in the presence of cyclosporin A. Basolateral to apical transport of rhodamine 123 decreases in the presence of cyclosporin A (80±5%) compared to the control (100±4%). Statistical significance was calculated by the Student's t-test; *, p<0.07.

Although the relative exclusion of the aforementioned lipophilic small molecules like colchicine, vincristine, and prazosin implies functionality of relevant BBB efflux transporters, we also assessed efflux transporter functionality and polarity through use of selective inhibitors. First, p-glycoprotein function in monocultured IMR90-4-derived BMECs was probed by use of rhodamine 123, a cell-permeable, fluorescent p-glycoprotein substrate (Table 7). There was a 1.4-fold increase in cellular accumulation of rhodamine 123 (decrease in efflux) in the presence of cyclosporin A, a known p-glycoprotein inhibitor, but not when Ko143 or MK 571, inhibitors of BCRP and the MRP family respectively, were used (Table 6), indicating the presence of functional p-glycoprotein in IMR90-4-derived BMECs (FIG. 5f [panel i]). When doxorubicin, a substrate for p-glycoprotein, BCRP, and the MRPs (Table 6), was added to IMR90-4-derived BMECs, its accumulation could be increased by the presence of cyclosporin A, Ko143, or MK 571, demonstrating the functional efflux activity of p-glycoprotein, BCRP, and the MRP family, respectively (FIG. 5f [panel i]). Next, directional transport assays using the IMR90-4-derived BMEC/astrocyte model demonstrated preferential efflux function in the brain-to-blood direction (basolateral to apical). For p-glycoprotein, transport of rhodamine 123 from the apical to basolateral chamber was 1.73-fold higher in the presence of cyclosporin A, but not Ko143 or MK 571, as a result of blocked efflux in the basolateral to apical direction (FIG. 5f [panel ii]). Conversely, transport of rhodamine 123 in the basolateral to apical direction was slightly decreased in cultures treated with cyclosporin A as a result of blocking p-glycoprotein extrusion of rhodamine 123 at the apical interface (FIG. 17). Similarly, transport of doxorubicin from the apical to basolateral chamber was increased 1.32-fold, 1.3-fold, and 1.17-fold by cyclosporin A, Ko143, and MK 571, respectively, indicating net functional polarization of p-glycoprotein, BCRP and MRP family efflux transporters (FIG. 5f [panel ii]).

TABLE 6

Efflux transporter substrates and inhibitors.

| Compounds[11-13] | Transporter recognition |
|---|---|
| Substrates | |
| Rhodamine 123 | MDR1 |
| Doxorubicin | MDR1, BCRP, MRP1, MRP2 |
| Inhibitors | |
| Cyclosporin A | MDR1 |
| Ko143 | BCRP |
| MK 571 | MRP family |

TABLE 7

Antibodies used for immunofluorescence and flow cytometry.

| Targeted antigen | Antibody description | Vendor | Dilution |
|---|---|---|---|
| PECAM-1 | Polyclonal rabbit | Thermo Fisher | 1:25 |
| von Willebrand Factor | Polyclonal rabbit | Dako | 1:100 |
| ZO-1 | Polyclonal rabbit | Invitrogen | 1:100 |
| Occludin | Mouse monoclonal | Invitrogen | 1:50 |
| Claudin-5 | Mouse monoclonal | Invitrogen | 1:200 |
| GLUT-1[a] | Polyclonal rabbit antiserum | N/A | 1:500 |
| GLUT-1[a] | Mouse monoclonal | Thermo Fisher | Clone SPM498, 1:100 |
| p-glycoprotein | Mouse monoclonal | Thermo Fisher | Clone F4, 1:25 |
| β-catenin | FITC-conjugated mouse monoclonal | BD Biosciences | 1:150 |
| βIII tubulin | Polyclonal rabbit | Sigma | 1:500 |
| Nestin[b] | Polyclonal rabbit | Millipore | 1:1000 |
| Nestin[b] | Mouse monoclonal | Millipore | 1:500 |
| GFAP | Polyclonal rabbit | Dako | 1:500 |
| α-smooth muscle actin | Mouse monoclonal | ARP | 1:100 |
| Digoxigenin | Mouse monoclonal | Sigma | 1:500 |

[a]The polyclonal GLUT-1 antiserum[7] was used for immunofluorescence only. The monoclonal GLUT-1 antibody was used for immunofluorescence and flow cytometry.
[b]The polyclonal nestin antibody was used for immunofluorescence and the monoclonal nestin antibody was used for immunofluorescence and flow cytometry.

Together, these data demonstrate function and polarization of efflux transporters. Importantly, the degree of polarization, as measured by increased flux in the presence of inhibitors, is consistent with that found in primary rodent BBB systems[57]. Overall, the composite of BBB gene and protein expression, tight junction fidelity, correlative permeability for small molecules, and polarized efflux transporter activity benchmarks the iPSC-derived BMECs as possessing significant BBB character.

Discussion

We have developed a novel system to differentiate human pluripotent stem cells into ECs with characteristic protein markers and functional properties of primary cultured brain microvascular endothelial cells. Animal BMECs have previously been the gold standard for in vitro blood-brain barrier models because they can be obtained in moderate yield while still maintaining barrier functions. Animal models have also been used to make significant strides in studies of BBB mechanisms and signaling pathways both in early development and adult regulation. However, due to inherent species differences (e.g. relative differences in transporter expression levels), these models are not assumed to always be directly predictive of human BBB properties, making them nonideal candidates for screening pharmaceuticals that will be taken up or excluded by the human BBB. Recently, an immortalized human brain endothelial cell line (hCMEC/D3) was developed for study of the human BBB, and while this model maintains some BBB functionality (active efflux transporters), it is known to possess poor barrier properties (low TEER and high permeability) and is thus unsuitable for screening purposes. The human pluripotent stem cell-derived BMECs are ultimately superior to both sources of cells because they are of human origin while possessing excellent barrier properties and BBB functionality. Table 9 summarizes various differences in barrier properties, functional transporters, and expression markers between each cell source compared to peripheral endothelial cells.

TABLE 9

In vitro phenotype of peripheral endothelial cells vs. blood-brain barrier endothelial cells

| Characteristic | Peripheral endothelium | hCMEC/D3 immortalized BBB endothelium | Primary rodent BBB endothelium | hPSC-derived BBB endothelium |
|---|---|---|---|---|
| Trans-endothelial electrical resistance (TEER) | Low (2-30 $\Omega \times cm^2$) | Low (30-199 $\Omega \times cm^2$) | Moderate (200-500 $\Omega \times cm^2$) | High (700-1450 $\Omega \times cm^2$) |
| Passive permeability to small hydrophilic molecules (i.e. sucrose) | High ($10^{-3}$ cm/min) | High ($10^{-3}$ cm/min) | Low ($10^{-5}$ cm/min) | Low ($10^{-5}$ cm/min) |
| Functional efflux transporters (p-glycoprotein, BCRP, MRP family) | No | Yes | Yes | Yes |
| Tight junction continuity | Low | Low | Moderate to high | High |
| Expression of tight junction protein claudin-5 | Yes | Yes | Yes | Yes |
| Expression of tight junction protein occludin | Variable | Yes | Yes | Yes |
| Expression of GLUT-1 | No | Yes | Yes | Yes |
| Expression of PLVAP | Yes | Unknown | Unknown | No |

Traditional methods of primary animal and human BMEC culture are employed by a limited number of laboratories because of their complexity. In contrast, the approaches described here for generating hPSC-derived BMECs capable of forming robust BBB models are of comparative ease and readily scalable given the efficiency of endothelial differentiation (>60%) and the capability to perform facile extracellular matrix-based purification. By comparison, other hPSC differentiation strategies utilizing embryoid bodies, OP9 co-culture, and 2D differentiation with endothelial factors have lower reported EC differentiation efficiencies (1-43%) and must be coupled with antibody-assisted purification methods to yield pure populations of Ecs[14-20, 28, 29]. In addition, none of these previous approaches has reported an EC population possessing organ-specific properties. In this study, BBB specification occurred in the presence of co-differentiating neural cells, which likely supplied many of the necessary cues normally provided by the embryonic brain microenvironment in vivo[24, 26, 27, 36, 47-49]. It is possible that co-differentiation strategies could also specify ECs of other lineages by providing organ-specific microenvironmental cues during development in vitro.

Importantly, the stem cell basis for this model presents a nearly unlimited source of human BMECs. We conservatively estimate that one vial of hPSCs could yield at least 6,000 BMEC-coated TRANSWELL™ filters.

In contrast, previous human models have been derived from primary tissue, which does not support high throughput assays due to yield, ethical constraints, tissue viability, and heterogeneity between isolations. Immortalized human BMECs eliminate concerns of yield, ethics, and heterogeneity but suffer from significantly decreased barrier properties (see Table 9 above), which limits their reliability in drug screening. Moreover, given that BMEC populations have been obtained from both hESC and iPSC lines derived via distinct reprogramming strategies (FIG. 2a), this hPSC-derived BMEC model could be readily adopted by the broader research community for studies of brain development, disease mechanisms, and drug delivery. The in vitro BBB specification process appears to involve Wnt/β-catenin signaling which is consistent with in vivo mechanisms of brain development demonstrated in mice[26, 27, 36].

This model will enable the elucidation of other molecular mechanisms leading to human BBB differentiation, a study previously intractable in humans. Information regarding human BBB development could be clinically relevant for promoting brain angiogenesis after stroke or inhibiting recruitment of blood vessels by brain tumors. Having shown the hPSC-derived BMECs possess excellent barrier characteristics with appropriate molecular exclusion and functional transport systems, it is anticipated this cellular platform will also be useful in drug permeability screens to either develop pharmaceuticals that can reach the brain or to limit the brain uptake of drugs that may have neurotoxic side effects.

Materials and Methods hPSC Culture and Differentiation

Human embryonic stem cells (H9)[11] and induced pluripotent stem cells (iPS(IMR90)-4[13], iPS-DF19-9-11T[35], and iPS-DF6-9-9T[35]) were maintained on irradiated mouse embryonic fibroblasts in standard unconditioned medium: Dulbecco's Modified Eagle's Medium/Ham's F12 containing 20% Knockout Serum Replacer (Invitrogen), 1×MEM nonessential amino acids (Invitrogen), 1 mM L-glutamine (Sigma), 0.1 mM β-mercaptoethanol (Sigma), and human basic fibroblast growth factor (bFGF, 4 ng/mL for hESCs and 100 ng/mL for iPSCs; Waisman Clinical Biomanufacturing Facility, University of Wisconsin-Madison). Prior to differentiation, cells were passaged onto Matrigel (BD Biosciences) in mTeSR1 medium (STEMCELL Technologies). After 2-3 days in mTeSR1 (ref. 32), medium was switched to unconditioned medium lacking bFGF (referred to as UM throughout manuscript) to initiate differentiation. Major morphological changes were observed by day 5-7 of UM treatment, at which point the medium was switched to endothelial cell (EC) medium: human Endothelial Serum-Free Medium (Invitrogen) supplemented with 20 ng/mL bFGF and 1% platelet-poor plasma derived bovine serum[34] (Biomedical Technologies, Inc.). Following 1-2 days of EC medium treatment, cells were dissociated with dispase (2 mg/mL; Invitrogen) and plated onto 12-well tissue culture polystyrene plates or 1.12 cm$^2$ TRANSWELL-CLEAR™ permeable inserts (0.4 μm pore size) coated with a mixture of collagen IV (400 μg/mL; Sigma) and fibronectin (100 μg/mL; Sigma). Culture plates were incubated with the coating for at least 30 min at 37° C., while the inserts were incubated for a minimum of 4 h at 37° C. One well of hPSCs from a standard 6-well tissue culture plate (9.6 cm$^2$) could be used to seed either three wells of a 12-well plate (11.4 cm$^2$) or four inserts (4.48 cm$^2$). Cells were then cultured in EC medium until they reached confluence (typically 1-2 days).

hPSC-Derived BMEC Co-Culture Experiments

For co-culture experiments, primary astrocytes were isolated as previously described[37]. Briefly, cortices were isolated from P6 neonatal Sprague Dawley rats (Harlan) and minced in Hank's Balanced Salt Solution (HBSS; Sigma). This tissue was digested in HBSS containing 0.5 mg/mL trypsin (Mediatech, Inc.) in a 37° C. shaker bath for 25 min, followed by digestion in HBSS containing 114 U/mL DNase I (Worthington Biochemical) in a 37° C. shaker bath for 5 min. After trituration and filtration, cells were cultured on collagen-I-coated flasks (100 μg/mL; Sigma) in DMEM containing 10% qualified heat-inactivated fetal bovine serum (FBS; Invitrogen), 10% heat-inactivated horse serum (Sigma), 2 mM L-glutamine, and 1% antibiotic-antimycotic (Invitrogen). Human embryonic kidney 293 cells (HEK cells; ATCC) were cultured in DMEM supplemented with 10% FBS, 1 mM sodium pyruvate (Sigma), 2 g/L sodium bicarbonate (Fisher Scientific), 30 mM HEPES (Sigma), and 1% antibiotic-antimycotic, and used as a non-neural cell control. Co-culture of hPSC-derived BMECs was initiated with primary rat astrocytes or HEK cells in either EC medium (called 1% PDS medium in Table 2) or 70:30 (v/v) DMEM/F12 (Sigma/Invitrogen) supplemented with 1% antibiotic-antimycotic, 2% B27 (Invitrogen), and 10% FBS[37] (called 10% FBS medium in Table 2). Trans-endothelial electrical resistance (TEER) measurements were performed using an EVOM voltohmmeter (World Precision Instruments) at the start of co-culture and every 24 h thereafter. The resistance value ($\Omega \times cm^2$) of an empty filter coated with collagen/fibronectin was subtracted from each measurement. Permeability coefficients ($P_e$) were evaluated after 24 h of co-culture as previously described[34]. For sodium fluorescein $P_e$ measurements, 10% FBS medium containing 1 μM sodium fluorescein solution was added to the apical chamber of the TRANSWELL™ filter. 200 μL aliquots were extracted from the basolateral chamber (which contains 1.5 mL of medium) every 30 min and replaced by fresh medium. Using a fluorescent plate reader and calibration curve, the flux of fluorescein to the bottom chamber and permeability coefficients were calculated as described by Calabria et al[34]. To determine the $P_e$ of radiolabeled ligands, compounds were diluted to 0.4 μCi in transport buffer (distilled water with 0.12 M NaCl, 25 mM NaHCO$_3$, 3 mM KCl, 2 mM MgSO$_4$, 2 mM CaCl$_2$, 0.4 mM K$_2$HPO$_4$, 1 mM HEPES, and 0.1% bovine serum albumin [BSA; Sigma]) and 0.5 mL were added to the upper chamber. 200 μL aliquots were extracted from the basolateral chamber every 15 min and replaced by fresh buffer. The rate of accumulation of radioactive ligand in the basolateral chamber over the course of 1 h was used to calculate $P_e$ values for [$^{14}$C]-sucrose, [$^3$H]-inulin, [$^3$H]-colchicine, [$^3$H]-diazepam, [$^3$H]-prazosin, [$^{14}$C]-glucose, and [$^3$H]-vincristine. [$^3$H]-vincristine was purchased from American Radiolabeled Chemicals, while all other radiolabeled compounds were acquired from PerkinElmer. All compound incubations were conducted at 37° C., and the radioactive permeability experiments were carried out on a rotator. Triplicate filters were used for all permeability studies and the values listed throughout the Results section are representative of a minimum of two biological replicates.

Efflux Transport Assays

P-glycoprotein, BCRP, and MRP functionality were assessed using rhodamine 123 (Sigma), a preferred substrate for p-glycoprotein, and [$^{14}$C]-doxorubicin (PerkinElmer), a substrate for all aforementioned efflux transporters. To assess activity, hPSC-derived BMEC monolayers (absent astrocyte co-culture) were pre-incubated for 30 min on a rotator at 37° C. with or without 5 µM cyclosporin A (Sigma), 1 µM Ko143 (Sigma), or 10 µM MK 571 (Sigma), which are inhibitors of p-glycoprotein, BCRP, or various MRPs, respectively. BMEC were then incubated with rhodamine 123 (10 µM) or doxorubicin (0.25 µCi) for 1 h on a rotator at 37° C. with or without inhibitors. Cells were then washed three times with ice-cold PBS and lysed with 5% Triton X-100 (TX-100; Fisher). Fluorescence (485 nm excitation and 530 nm emission) was measured using a plate reader and normalized to cell counts obtained using a hemocytometer, while radioactivity was measured using a liquid scintillation counter. To quantify apical-to-basolateral transport, hPSC-derived BMEC monolayers on TRANSWELL™ filters were co-cultured with astrocytes for 24 h and then pre-incubated with or without inhibitors in their original co-culture medium containing 10% FBS for 60 min, followed by addition of rhodamine 123 or doxorubicin to the upper chamber. After another 60 min, aliquots were extracted from the bottom chamber and transport was quantified on a plate reader or scintillation counter. To quantify basolateral-to-apical transport, hPSC-derived BMEC monolayers on TRANSWELL™ filters were pre-incubated with or without cyclosporin A in co-culture medium containing 10% FBS for 60 min, followed by addition of rhodamine 123 to the lower chamber. After 3 h, aliquots were extracted from the upper chamber and fluorescence quantified on a plate reader. All measurements of accumulation and transport were normalized to accumulation and transport in the absence of inhibitor. Rhodamine accumulation or transport studies were carried out in fresh co-culture medium containing 10% FBS, while doxorubicin studies were conducted in transport buffer (described above). Sucrose permeability and TEER measurements were used to confirm monolayer integrity in the presence of inhibitors.

Tube-Forming and Acetylated Low-Density Lipoprotein (LDL) Uptake Assays 24-well tissue culture plates were coated with 500 µL of Matrigel for 1 h at 37° C. Collagen/fibronectin-purified hPSC-derived BMECs were dissociated using trypsin, and 100,000 cells were plated into each Matrigel-coated well in EC medium supplemented with 40 ng/mL VEGF (R&D Systems) and imaged after 12 h. A control sample of cells lacking VEGF was also employed. For acetylated LDL uptake, purified hPSC-derived BMECs were incubated with 10 µg/mL acetylated LDL conjugated to Alexa Fluor 488 (Invitrogen) for 4 h at 37° C., washed twice with PBS, and visualized immediately with an Olympus epifluorescence microscope. Images were taken using a Diagnostic Instruments camera run by MetaVue software.

Immunocytochemistry/In Situ Hybridization

Cells were washed once with PBS and fixed in either 2% paraformaldehyde or 100% ice-cold methanol for 15 min. The cells were then blocked with 40% goat serum in PBS (40% PBSG). If probing for an intracellular antigen, 0.1% TX-100 was present in the 40% PBSG. The cells were then incubated in 40% PBSG containing primary antibody (see Table 5 for list) for one h at room temperature. After three washes in PBS, cells were incubated in 40% PBSG containing goat anti-rabbit Texas Red (1:500; Invitrogen) or goat anti-mouse Alexa 488 (1:500; Invitrogen). Cell nuclei were labeled with 300 nM 4',6-Diamidino-2-pheny-lindol-dihydrochloride (DAPI) for 10 min. Cells were washed three times in PBS and visualized. In situ hybridization for detection of WNT7A and WNT7B transcripts was conducted similar to the method described by Planell-Saguer et al[58]. Briefly, cells were washed once with PBS and fixed in 2% paraformaldehyde for 10 min, followed by permeabilization in PBS containing 0.1% TX-100 for 5 min. Pre-hybridization was performed with a water-based solution containing 3% BSA and 4× saline-sodium citrate buffer (SSC; Fisher), followed by a 1 h hybridization in 4×SSC and 10% dextran sulfate (Fisher) at room temperature. Digoxigenin-labeled locked nucleic acid probes were purchased from Exiqon (sequences found in Table 6). Following three washes in 4×SSC/0.1% Tween-20, one wash in 2×SSC, one wash in 1×SSC, and one wash in PBS (all washes conducted at 50° C.), cells were blocked in PBS containing 4% BSA for 20 min and labeled overnight at 4° C. with a monoclonal anti-digoxigenin antibody (Sigma). Secondary antibody and DAPI labeling were carried out as described above.

Flow Cytometry

Cells were harvested via Accutase (Invitrogen) incubation for 2-3 min, fixed in 100% ice-cold methanol for 20 min, and blocked with 40% PBSG for 20 min at room temperature. Primary antibody labeling (Table 5) was performed in 10% PBSG for 1 h at room temperature. IgG controls were used at the same concentration. After a wash with 5% FBS in PBS, secondary antibodies (goat anti-rabbit Alexa 488 and goat anti-mouse Alexa 647; 1:200) in 10% PBSG were added to each sample for 30 min at room temperature. After two washes with 5% FBS in PBS, the samples were analyzed on a FACScaliber flow cytometer. PECAM-1$^+$ events were quantified using a PECAM-1/forward scatter dot plot referenced to a rabbit IgG control. GLUT-1$^+$ events were quantified using a GLUT-1/forward scatter dot plot referenced to a 4D UM culture that lacked BMECs. Events that were found in both of these positive gates were classified as PECAM-1$^+$/GLUT-1$^+$ cells. βIII tubulin and nestin expression were quantified against rabbit and mouse IgG controls, respectively. Data are presented as two-dimensional dot plots with color codes to indicate events within each gate. For inhibition of BMEC differentiation, 10 µM of XAV-939 (Sigma) or equivalent DMSO vehicle control was added to IMR90-4 iPSCs starting at day 2 of UM treatment, and PECAM-1/GLUT-1 expression were evaluated as described above.

Reverse-Transcription Polymerase Chain Reaction (RT-PCR), Quantitative RT-PCR, and Gel Electrophoresis Cells were differentiated as previously described. For inhibition of Wnt signaling, cells were treated with 250 ng/mL of mouse secreted frizzled-related protein 2 (SFRP2; R&D Systems) in UM for 4 days, followed by 750 ng/mL of SFRP2 in UM for an additional 3 days, or with 10 µM XAV or equivalent volume of DMSO vehicle control starting at day 2 of UM treatment. For RNA collection, cells were washed once with PBS and dissociated with trypsin or accutase. Total RNA was extracted using an RNeasy Mini Kit (Qiagen) according to the manufacturer's instructions. cDNA was generated from 1 µg of RNA using Omniscript reverse transcriptase (Qiagen) and oligo-dT primers (Invitrogen). Quantitative PCR (qPCR) was then performed using 1 µL of cDNA and iQ SYBR Green Supermix (Bio-Rad) on an iCycler (Bio-Rad). RT-PCR was also performed using GoTaq Green Master Mix (Promega). Primer sequences are supplied in Table 8. Relative expression was quantified using the comparative cycle threshold ($C_T$) method, normalizing to glyceraldehyde-3-phosphate dehydrogenase (GAPDH) expression. Fold difference was calculated as $x^{-\Delta\Delta C_T}$, where x refers to primer efficiency calculated according LinRegPCR version 12.3[59]. Transcript amplification was analyzed by 2% agarose gel electrophoresis of the qPCR or RT-PCR products.

TABLE 8

Primers used for RT-PCR and qPCR.

| Gene[a] | Forward sequence | Reverse sequence |
|---|---|---|
| GAPDH | CACCGTCAAGGCTGAGAACG (SEQ ID NO: 1) | GCCCCACTTGATTTTGGAGG (SEQ ID NO: 2) |
| SLC2A1 | ACGCTCTGATCCCTCTCAGT (SEQ ID NO: 3) | GCAGTACACACCGTAGATGAAG (SEQ ID NO: 4) |
| ABCB1 | TGAATCTGGAGGAAGACATGAC (SEQ ID NO: 5) | CCAGGCACCAAAATGAAACC (SEQ ID NO: 6) |
| LEF1 | CAGATGTCAACTCCAAACAAGG (SEQ ID NO: 7) | GATGGGATATACAGGCTGACC (SEQ ID NO: 8) |
| STRA6 | TTTGGAATCGTGCTCTCCG (SEQ ID NO: 9) | AAGGTGAGTAAGCAGGACAAG (SEQ ID NO: 10) |
| FZD4 | TACCTCACAAAACCCCCATCC (SEQ ID NO: 11) | GGCTGTATAAGCCAGCATCAT (SEQ ID NO: 12) |
| FZD6 | TCGTCAGTACCATATCCCATG (SEQ ID NO: 13) | CCCATTCTGTGCATGTCTTTT (SEQ ID NO: 14) |
| FZD7 | GATGATAACGGCGATGTGA (SEQ ID NO: 15) | AACAAAGCAGCCACCGCAGAC (SEQ ID NO: 16) |
| FST | GTTCATGGAGGACCGCAGTG (SEQ ID NO: 17) | TCTTCTTGTTCATTCGGCATT (SEQ ID NO: 18) |
| APCDD1 | GGAGTCACAGTGCCATCACAT (SEQ ID NO: 19) | CCTGACCTTACTTCACAGCCT (SEQ ID NO: 20) |
| CDH5 | CGCAATAGACAAGGACATAACAC (SEQ ID NO: 21) | GGTCAAACTGCCCATACTTG (SEQ ID NO: 22) |
| VWF | CCCGAAAGGCCAGGTGTA (SEQ ID NO: 23) | AGCAAGCTTCCGGGGACT (SEQ ID NO: 24) |
| LDLR | GCCATTGTCGTCTTTATGTC (SEQ ID NO: 25) | AAACACATACCCATCAACGA (SEQ ID NO: 26) |
| SLC7A5 | TTAAAGTAGATCACCTCCTCGA (SEQ ID NO: 27) | GGATGAGATTCGTACCAGAG (SEQ ID NO: 28) |
| SLC16A1 | GGTGTTTCTTAGTAGTTATGGG (SEQ ID NO: 29) | TCTTATTGGCTTTGTGTTGG (SEQ ID NO: 30) |
| INSR | TGTTCATCCTCTGATTCTCTG (SEQ ID NO: 31) | GCTTAGATGTTCCCAAAGTC (SEQ ID NO: 32) |
| LEPR | GGAAATCACACGAAATTCAC (SEQ ID NO: 33) | GCACGATATTTACTTTGCTC (SEQ ID NO: 34) |
| BCAM | GCTTTCCTTACCTCTAAACAG (SEQ ID NO: 35) | GAAGGTGATAGAACTGAGCG (SEQ ID NO: 36) |
| SLC38A5 | TGTCAGTGTTCAACCTCAG (SEQ ID NO: 37) | GTGGATGGAGTAGGACGA (SEQ ID NO: 38) |
| SLC1A1 | GTTATTCTAGGTATTGTGCTGG (SEQ ID NO: 39) | CTGATGAGATCTAACATGGC (SEQ ID NO: 40) |
| ABCC1 | AATAGAAGTGTTGGGCTGAG (SEQ ID NO: 41) | CGAGACACCTTAAAGAACAG (SEQ ID NO: 42) |
| ABCC2 | ATATAAGAAGGCATTGACCC (SEQ ID NO: 43) | ATCTGTAGAACACTTGACCA (SEQ ID NO: 44) |
| ABCC4 | AATCTACAACTCGGAGTCCA (SEQ ID NO: 45) | CAAGCCTCTGAATGTAAATCC (SEQ ID NO: 46) |
| ABCC5 | TCACTACATTAAGACTCTGTCC (SEQ ID NO: 47) | GGATACTTTCTTTAGGACGAGAG (SEQ ID NO: 48) |
| AGER | GTAGATTCTGCCTCTGAACTC (SEQ ID NO: 49) | CTTCACAGATACTCCCTTCTC (SEQ ID NO: 50) |
| SLC21A14[b] | AAAGATGTGGAAGTAGAGGA (SEQ ID NO: 51) | ATGCTTAGGAGAATTGACAC (SEQ ID NO: 52) |
| PLVAP[b] | CAATGCAGAGATCAATTCAAGG (SEQ ID NO: 53) | ACGCTTTCCTTATCCTTAGTG (SEQ ID NO: 54) |
| TFRC | GCACAGCTCTCCTATTGAAAC (SEQ ID NO: 55) | GGTATCCCTCTAGCCATTCAG (SEQ ID NO: 56) |
| LRP1 | GACTACATTGAATTTGCCAGCC (SEQ ID NO: 57) | TCTTGTGGGCTCGGTTAATG (SEQ ID NO: 58) |
| WNT7A | CGGGAGATCAAGCAGAATG (SEQ ID NO: 59) | CGTGGCACTTACATTCCAG (SEQ ID NO: 60) |
| WNT7B | GCTTCGTCAAGTGCAACA (SEQ ID NO: 61) | GGAGTGGATGTGCAAAATG (SEQ ID NO: 62) |
| WNT7A[c] | TGGAACAGAATAGTTGAGGGCT (SEQ ID NO: 63) | N/A |
| WNT7B[c] | AGCCAAGGGACAGTGCGAGTGT (SEQ ID NO: 64) | N/A |

[a]For genes with multiple transcript variants (e.g. LEPR, BCAM), the primers were designed to encompass all transcript variants and not one single transcript isoform.
[b]Fidelity of SLC21A14 and PLVAP primers was confirmed using HUVECs because these genes were not expressed in the IMR90-4-derived BMECs.
[c]DIG-labeled probe sequences used for fluorescence in situ hybridization and DIG-labeled sense probes were used as controls.

Measurement of BMEC Properties

Co-culture of iPSC-derived BMECs was initiated with primary rat astrocytes or human embryonic kidney 293 cells in either EC media (defined above) or 70:30 (v/v) DMEM/F12 (Sigma/Invitrogen) supplemented with 1% (v/v) antibiotic-antimycotic, 2% (v/v) B27, and 10% (v/v) FBS. Transendothelial electrical resistance measurements were performed using an EVOM voltohmmeter (World Precision Instruments, Sarasota, Fla., USA) at the start of co-culture and approximately every 24 hours thereafter. The resistance value (ohms×cm$^2$) of an empty filter coated with collagen/fibronectin was subtracted from each measurement. Permeability coefficients were evaluated after 24 hours of co-culture as previously described. Briefly, a solution of 1 μM sodium fluorescene was added to the apical chamber of the TRANSWELL™ filter and 200 µL aliquots were extracted from the basolateral chamber every 30 minutes. Using a fluorescent plate reader and calibration curve, the rate of fluorescene influx to the bottom chamber was calculated, and final values for permeability coefficients were then calculated according to Calabria et al.[34].

To assess p-glycoprotein functionality, standard rhodamine 123 (Sigma) efflux assays were employed. For the rhodamine 123 accumulation assay, confluent IMR90-derived monolayers were pre-incubated with or without 5 µM cyclosporin A (Sigma) at 37° C. for 30 minutes with shaking. 10 µM rhodamine 123 was then added with or without inhibitor and the cells were incubated at 37° C. for 60 minutes with shaking. Cells were then washed three times with ice-cold PBS and lysed with 5% TX-100. Fluorescence was measured using the plate reader. Separate wells of cells incubated with or without inhibitor were trypsinized and counted with a hemocytometer to normalize the fluorescent readings to cell number. For the apical-to-basolateral transport study, the cells were pre-incubated with or without 5 µM cyclosporin A for 60 minutes, followed by addition of 10 µM rhodamine 123 to the upper chamber. After another 60 minutes, aliquots were extracted from the bottom chamber and analyzed on the plate reader. For the basolateral-to-apical transport study, the cells were pre-incubated with or without 5 µM cyclosporin A for 60 minutes, followed by addition of 10 µM rhodamine 123 to the lower chamber. After 3 hours, aliquots were extracted from the upper chamber and analyzed on the plate reader. All samples were normalized to the non-inhibitor values. All TEER, permeability, and efflux assay experiments were performed with triplicate filters or wells from which the reported averages and standard deviations are calculated.

Freeze-Fracture Electron Microscopy

After 24 h of co-culture with rat astrocytes, IMR90-4-derived BMECs were washed once with PBS, fixed in 1.5% gluteraldehyde (Sigma) for 60 min, washed several times with PBS, cryoprotected with glycerol (30%), scraped from the filters, loaded into gold specimen carriers (Bal-Tec part # LZ 02125 VN), and plunged in liquid ethane. Frozen specimens were transferred to a Balzers 301 Freeze Fracture Apparatus for fracturing and 1 min of sublimation at −110° C. Etched fracture surfaces were replicated with platinum at 45° supported by carbon deposited from 90°. Replicas were cleaned for 1 h using commercial household bleach followed by rinsing with double distilled water. Bare 400 mesh copper grids were used to pick up the cleaned replicas. Images were obtained using a JEOL 1230 TEM equipped with a Gatan Model 894 2 k×2 k CCD camera.

Inhibition of Wnt Signaling

PNU-74654 was purchased from Sigma and SFRP2 was purchased from R&D Systems. SFRP2 (250 ng/mL) or PNU-74654 (5 µM) was added for the first 4 days of UM treatment. Concentrations were then increased to 750 ng/mL and 10 µM, respectively, for the remainder of UM treatment. For flow cytometry, SFRP2 (250 ng/mL) and PNU-74654 (5 µM) were combined in UM. The concentrations were again increased to 750 ng/mL and 10 µM for the later-stage UM and EC media treatments.

REFERENCES

1. Butt, A. M., Jones, H. C. & Abbott, N. J. Electrical resistance across the blood-brain barrier in anaesthetized rats: a developmental study. *The Journal of physiology* 429, 47-62 (1990).
2. Pardridge, W. M. Blood-brain barrier drug targeting: the future of brain drug development. *Molecular interventions* 3, 90-105, 151 (2003).
3. Weiss, N., Miller, F., Cazaubon, S. & Couraud, P. O. The blood-brain barrier in brain homeostasis and neurological diseases. *Biochimica et biophysica acta* 1788, 842-857 (2009).
4. Deli, M. A., Abraham, C. S., Kataoka, Y. & Niwa, M. Permeability studies on in vitro blood-brain barrier models: physiology, pathology, and pharmacology. *Cellular and molecular neurobiology* 25, 59-127 (2005).
5. Syvanen, S. et al. Species differences in blood-brain barrier transport of three positron emission tomography radioligands with emphasis on P-glycoprotein transport. *Drug metabolism and disposition: the biological fate of chemicals* 37, 635-643 (2009).
6. Warren, M. S. et al. Comparative gene expression profiles of ABC transporters in brain microvessel endothelial cells and brain in five species including human. *Pharmacol Res* 59, 404-413 (2009).
7. Cecchelli, R. et al. Modelling of the blood-brain barrier in drug discovery and development. *Nat Rev Drug Discov* 6, 650-661 (2007).
8. Weksler, B. B. et al. Blood-brain barrier-specific properties of a human adult brain endothelial cell line. *Faseb J* 19, 1872-1874 (2005).
9. Forster, C. et al. Differential effects of hydrocortisone and TNFalpha on tight junction proteins in an in vitro model of the human blood-brain barrier. *The Journal of physiology* 586, 1937-1949 (2008).
10. Man, S. et al. Human brain microvascular endothelial cells and umbilical vein endothelial cells differentially facilitate leukocyte recruitment and utilize chemokines for T cell migration. *Clinical & developmental immunology* 2008, 384982 (2008).
11. Thomson, J. A. et al. Embryonic stem cell lines derived from human blastocysts. *Science* (New York, N.Y. 282, 1145-1147 (1998).
12. Takahashi, K. et al. Induction of pluripotent stem cells from adult human fibroblasts by defined factors. *Cell* 131, 861-872 (2007).
13. Yu, J. et al. Induced pluripotent stem cell lines derived from human somatic cells. *Science* (New York, N.Y. 318, 1917-1920 (2007).
14. Goldman, O. et al. A boost of BMP4 accelerates the commitment of human embryonic stem cells to the endothelial lineage. *Stem cells* (Dayton, Ohio) 27, 1750-1759 (2009).
15. James, D. et al. Expansion and maintenance of human embryonic stem cell-derived endothelial cells by TGFbeta inhibition is Id1 dependent. *Nature biotechnology* 28, 161-166.
16. Levenberg, S., Golub, J. S., Amit, M., Itskovitz-Eldor, J. & Langer, R. Endothelial cells derived from human embryonic stem cells. *Proceedings of the National Academy of Sciences of the United States of America* 99, 4391-4396 (2002).
17. Nakahara, M. et al. High-efficiency production of subculturable vascular endothelial cells from feeder-free human embryonic stem cells without cell-sorting technique. *Cloning and stem cells* 11, 509-522 (2009).
18. Wang, L. et al. Endothelial and hematopoietic cell fate of human embryonic stem cells originates from primitive endothelium with hemangioblastic properties. *Immunity* 21, 31-41 (2004).

19. Choi, K. D. et al. Hematopoietic and endothelial differentiation of human induced pluripotent stem cells. *Stem cells* (Dayton, Ohio) 27, 559-567 (2009).
20. Vodyanik, M. A., Bork, J. A., Thomson, J. A. & Slukvin, II Human embryonic stem cell-derived CD34+ cells: efficient production in the coculture with OP9 stromal cells and analysis of lymphohematopoietic potential. *Blood* 105, 617-626 (2005).
21. Cleaver, O. & Melton, D. A. Endothelial signaling during development. *Nature medicine* 9, 661-668 (2003).
22. Bauer, H. et al. Ontogenic expression of the erythroid-type glucose transporter (Glut 1) in the telencephalon of the mouse: correlation to the tightening of the blood-brain barrier. *Brain Res Dev Brain Res* 86, 317-325 (1995).
23. Bauer, H. C. et al. Neovascularization and the appearance of morphological characteristics of the blood-brain barrier in the embryonic mouse central nervous system. *Brain Res Dev Brain Res* 75, 269-278 (1993).
24. Daneman, R., Zhou, L., Kebede, A. A. & Barres, B. A. Pericytes are required for blood-brain barrier integrity during embryogenesis. *Nature* 468, 562-566.
25. Stewart, P. A. & Hayakawa, K. Early ultrastructural changes in blood-brain barrier vessels of the rat embryo. *Brain Res Dev Brain Res* 78, 25-34 (1994).
26. Daneman, R. et al. Wnt/beta-catenin signaling is required for CNS, but not non-CNS, angiogenesis. *Proceedings of the National Academy of Sciences of the United States of America* 106, 641-646 (2009).
27. Stenman, J. M. et al. Canonical Wnt signaling regulates organ-specific assembly and differentiation of CNS vasculature. *Science* (New York, N.Y. 322, 1247-1250 (2008).
28. Kane, N. M. et al. Derivation of endothelial cells from human embryonic stem cells by directed differentiation: analysis of microRNA and angiogenesis in vitro and in vivo. *Arteriosclerosis, thrombosis, and vascular biology* 30, 1389-1397.
29. Wang, Z. Z. et al. Endothelial cells derived from human embryonic stem cells form durable blood vessels in vivo. *Nature biotechnology* 25, 317-318 (2007).
30. Daadi, M. M., Maag, A. L. & Steinberg, G. K. Adherent self-renewable human embryonic stem cell-derived neural stem cell line: functional engraftment in experimental stroke model. *PloS one* 3, e1644 (2008).
31. Ying, Q. L., Stavridis, M., Griffiths, D., Li, M. & Smith, A. Conversion of embryonic stem cells into neuroectodermal precursors in adherent monoculture. *Nature biotechnology* 21, 183-186 (2003).
32. Ludwig, T. E. et al. Feeder-independent culture of human embryonic stem cells. *Nature methods* 3, 637-646 (2006).
33. Daneman, R. et al. The mouse blood-brain barrier transcriptome: a new resource for understanding the development and function of brain endothelial cells. *PloS one* 5, e13741.
34. Calabria, A. R., Weidenfeller, C., Jones, A. R., de Vries, H. E. & Shusta, E. V. Puromycin-purified rat brain microvascular endothelial cell cultures exhibit improved barrier properties in response to glucocorticoid induction. *Journal of neurochemistry* 97, 922-933 (2006).
35. Yu, J. et al. Human induced pluripotent stem cells free of vector and transgene sequences. *Science* (New York, N.Y 324, 797-801 (2009).
36. Liebner, S. et al. Wnt/beta-catenin signaling controls development of the blood-brain barrier. *The Journal of cell biology* 183, 409-417 (2008).
37. Weidenfeller, C., Svendsen, C. N. & Shusta, E. V. Differentiating embryonic neural progenitor cells induce blood-brain barrier properties. *Journal of neurochemistry* 101, 555-565 (2007).
38. Xu, Q. et al. Vascular development in the retina and inner ear: control by Norrin and Frizzled-4, a high-affinity ligand-receptor pair. *Cell* 116, 883-895 (2004).
39. Ye, X. et al. Norrin, frizzled-4, and Lrp5 signaling in endothelial cells controls a genetic program for retinal vascularization. *Cell* 139, 285-298 (2009).
40. Robitaille, J. et al. Mutant frizzled-4 disrupts retinal angiogenesis in familial exudative vitreoretinopathy. *Nature genetics* 32, 326-330 (2002).
41. Bouillet, P. et al. Developmental expression pattern of Stra6, a retinoic acid-responsive gene encoding a new type of membrane protein. *Mechanisms of development* 63, 173-186 (1997).
42. Kawaguchi, R. et al. A membrane receptor for retinol binding protein mediates cellular uptake of vitamin A. *Science* (New York, N.Y. 315, 820-825 (2007).
43. Szeto, W. et al. Overexpression of the retinoic acid-responsive gene Stra6 in human cancers and its synergistic induction by Wnt-1 and retinoic acid. *Cancer research* 61, 4197-4205 (2001).
44. Shimomura, Y. et al. APCDD1 is a novel Wnt inhibitor mutated in hereditary hypotrichosis simplex. *Nature* 464, 1043-1047.
45. Dravid, G. et al. Defining the role of Wnt/beta-catenin signaling in the survival, proliferation, and self-renewal of human embryonic stem cells. *Stem cells* (Dayton, Ohio) 23, 1489-1501 (2005).
46. Huang, S. M. et al. Tankyrase inhibition stabilizes axin and antagonizes Wnt signalling. *Nature* 461, 614-620 (2009).
47. Anderson, K. D. et al. Angiogenic sprouting into neural tissue requires Gpr124, an orphan G protein-coupled receptor. *Proceedings of the National Academy of Sciences of the United States of America* 108, 2807-2812.
48. Cullen, M. et al. GPR124, an orphan G protein-coupled receptor, is required for CNS-specific vascularization and establishment of the blood-brain barrier. *Proceedings of the National Academy of Sciences of the United States of America* 108, 5759-5764.
49. Kuhnert, F. et al. Essential regulation of CNS angiogenesis by the orphan G protein-coupled receptor GPR124. *Science* (New York, N.Y. 330, 985-989.
50. Vittet, D. et al. Embryonic stem cells differentiate in vitro to endothelial cells through successive maturation steps. *Blood* 88, 3424-3431 (1996).
51. Rubin, L. L. et al. A cell culture model of the blood-brain barrier. *The Journal of cell biology* 115, 1725-1735 (1991).
52. Liebner, S., Kniesel, U., Kalbacher, H. & Wolburg, H. Correlation of tight junction morphology with the expression of tight junction proteins in blood-brain barrier endothelial cells. *European journal of cell biology* 79, 707-717 (2000).
53. Hartz, A. M. & Bauer, B. ABC Transporters in the CNS—An Inventory. *Current pharmaceutical biotechnology* 12, 656-673.
54. Roberts, L. M. et al. Expression of the thyroid hormone transporters monocarboxylate transporter-8 (SLC16A2) and organic ion transporter-14 (SLCO1C1) at the blood-brain barrier. *Endocrinology* 149, 6251-6261 (2008).
55. Uchida, Y. et al. Quantitative targeted absolute proteomics of human blood-brain barrier transporters and receptors. *Journal of neurochemistry* 117, 333-345.

56. Muruganandam, A., Tanha, J., Narang, S. & Stanimirovic, D. Selection of phage-displayed llama single-domain antibodies that transmigrate across human blood-brain barrier endothelium. *Faseb J* 16, 240-242 (2002).
57. Perriere, N. et al. A functional in vitro model of rat blood-brain barrier for molecular analysis of efflux transporters. *Brain Res* 1150, 1-13 (2007).
58. de Planell-Saguer, M., Rodicio, M. C. & Mourelatos, Z. Rapid in situ codetection of noncoding RNAs and proteins in cells and formalin-fixed paraffin-embedded tissue sections without protease treatment. *Nature protocols* 5, 1061-1073.
59. Tuomi, J. M., Voorbraak, F., Jones, D. L. & Ruijter, J. M. Bias in the Cq value observed with hydrolysis probe based quantitative PCR can be corrected with the estimated PCR efficiency value. *Methods (San Diego, Calif.* 50, 313-322.
60. Kleinman et al., Biochemistry, 1982. 21(24): p. 6188-6193.
61. Kleinman et al., Biochemistry, 1986. 25(2): p. 312-318.
62. Vikicevic et al., Exp Cell Res, 1992. 202(1): p. 1-8.
63. Azarin et al., Biochem Eng J, 2010. 48(3): p. 378.
64. Ueno, Curr Med Chem, 2007. 14(11): p. 1199-1206.
65. Pardridge et al., J Biol Chem, 1990. 265(29): p. 18035-18040.
66. Sun et al., Adv Drug Deliv Rev, 2003. 55(1): p. 83-105.
67. Abbott et al., Nat Rev Neurosci, 2006. 7(1): p. 41-53.
68. T. E. Ludwig, M. E. Levenstein, J. M. Jones, W. T. Berggren, E. R. Mitchen, J. L. Frane, L. J. Crandall, C. A. Daigh, K. R. Conard, M. S. Piekarczyk, R. A. Llanas, J. A. Thomson, Derivation of human embryonic stem cells in defined conditions, Nat Biotechnol 24, 185-187 (2006).
69. Aasen, T., Raya, A., Barrero, M. J., et al., Efficient and rapid generation of induced pluripotent stem cells from human keratinocytes. *Nat Biotechnol* 26, 1276-1284 (2008).
70. Aoki, T., Ohnishi, H., Oda, Y., et al., Generation of induced pluripotent stem cells from human adipose-derived stem cells without c-MYC. *Tissue Eng Part A* 16, 2197-2206, (2010).
71. Banito, A., Rashid, S. T., Acosta, J. C., et al., Senescence impairs successful reprogramming to pluripotent stem cells. *Genes Dev* 23: 2134-2139 (2009).
72. Byrne, J. A., Nguyen, H. N. and Reijo Pera, R. A., Enhanced generation of induced pluripotent stem cells from a subpopulation of human fibroblasts. *PLoS One* 4: e7118 (2009).
73. Cai, J., Li, W., Su, H., et al., Generation of human induced pluripotent stem cells from umbilical cord matrix and amniotic membrane mesenchymal cells. *J Biol Chem* 285: 11227-11234 (2010).
74. Carey, B. W., Markoulaki, S., Hanna, J., et al., Reprogramming of murine and human somatic cells using a single polycistronic vector. *Proc Natl Acad Sci USA* 106: 157-162 (2009).
75. Chang, C. W., Lai, Y. S., Pawlik, K. M., et al., Polycistronic Lentiviral Vector for "Hit and Run" Reprogramming of Adult Skin Fibroblasts to Induced Pluripotent Stem Cells. *Stem Cells* 27: 1042-1049 (2009).
76. Chen, A. E., Egli, D., Niakan, K., et al., Optimal timing of inner cell mass isolation increases the efficiency of human embryonic stem cell derivation and allows generation of sibling cell lines. *Cell Stem Cell* 4: 103-106 (2009).
77. Chung, Y., Klimanskaya, I., Becker, S., et al., Human embryonic stem cell lines generated without embryo destruction. *Cell Stem Cell* 2: 113-117 (2009).
78. Geens, M., Mateizel, I., Sermon, K., et al., Human embryonic stem cell lines derived from single blastomeres of two 4-cell stage embryos. *Hum Reprod* 24: 2709-2717 (2009).
79. Giorgetti, A., Montserrat, N., Aasen, T., et al., Generation of induced pluripotent stem cells from human cord blood using OCT4 and SOX2. *Cell Stem Cell* 5: 353-357 (2009).
80. Haase, A., Olmer, R., Schwanke, K., et al., Generation of induced pluripotent stem cells from human cord blood. *Cell Stem Cell* 5: 434-441 (2009).
81. Huangfu, D., Osafune, K., Maehr, R., et al., Induction of pluripotent stem cells from primary human fibroblasts with only Oct4 and Sox2. *Nat Biotechnol* 26: 1269-1275 (2008).
82. Kaji, K., Norrby, K., Paca, A., et al., Virus-free induction of pluripotency and subsequent excision of reprogramming factors. *Nature* 458: 771-775 (2009).
83. Kim, D., Kim, C. H., Moon, J. I., et al., Generation of human induced pluripotent stem cells by direct delivery of reprogramming proteins. *Cell Stem Cell* 4: 472-476 (2009).
84. Kim, J. B., Greber, B., Arauzo-Bravo, M. J., et al., Direct reprogramming of human neural stem cells by OCT4. *Nature* 461: 649-653 (2009).
85. Klimanskaya, I., Chung, Y., Becker, S., Lu, S. J. and Lanza, R., Human embryonic stem cell lines derived from single blastomeres. *Nature* 444: 481-485 (2006).
86. Lerou, P. H., Yabuuchi, A., Huo, H., et al., Human embryonic stem cell derivation from poor-quality embryos. *Nat Biotechnol* 26: 212-214 (2008).
87. Li, W., Zhou, H., Abujarour, R., et al., Generation of human-induced pluripotent stem cells in the absence of exogenous Sox2. *Stem Cells* 27: 2992-3000 (2009).
88. Lin, T., Ambasudhan, R., Yuan, X., et al., A chemical platform for improved induction of human iPSCs. *Nat Methods* 6: 805-808 (2009).
89. Loh, Y. H., Agarwal, S., Park, I. H., et al., Generation of induced pluripotent stem cells from human blood. *Blood* 113: 5476-5479 (2009).
90. Maherali, N., Ahfeldt, T., Rigamonti, A., et al., A high-efficiency system for the generation and study of human induced pluripotent stem cells. *Cell Stem Cell* 3: 340-345 (2009).
91. Nagata, S., Toyoda, M., Yamaguchi, S., et al., Efficient reprogramming of human and mouse primary extra-embryonic cells to pluripotent stem cells. *Genes Cells* 14: 1395-1404 (2009).
92. Nakagawa, M., Koyanagi, M., Tanabe, K., et al., Generation of induced pluripotent stem cells without Myc from mouse and human fibroblasts. *Nat Biotechnol* 26: 101-106 (2008).
93. Papapetrou, E. P., Tomishima, M. J., Chambers, S. M., et al., Stoichiometric and temporal requirements of Oct4, Sox2, Klf4, and c-Myc expression for efficient human iPSC induction and differentiation. *Proc Natl Aced Sci USA* 106: 12759-64 (2009).
94. Park, I. H., Zhao, R., West, J. A., et al., Reprogramming of human somatic cells to pluripotency with defined factors. *Nature* 451: 141-146 (2008).
95. Revazova, E. S., Turovets, N. A., Kochetkova, O. D., et al., HLA homozygous stem cell lines derived from human parthenogenetic blastocysts. *Cloning Stem Cells* 10: 11-24 (2008).

96. Rodriguez-Piza, I., Richaud-Patin, Y., Vassena, R., et al., Reprogramming of human fibroblasts to induced pluripotent stem cells under xeno-free conditions. *Stem Cells* 28: 36-44 (2010).
97. Ross, P. J., Suhr, S., Rodriguez, R. M., et al, Human Induced Pluripotent Stem Cells Produced Under Xeno-Free Conditions. *Stem Cells Dev* 19: 1221-1229 (2009).
98. Takenaka, C., Nishishita, N., Takada, N., Jakt, L. M. and Kawamata, S., Effective generation of iPS cells from CD34+ cord blood cells by inhibition of p53. *Exp Hematol* 38: 154-62 (2010).
99. Ye, Z., Zhan, H., Mali, P., et al., Human-induced pluripotent stem cells from blood cells of healthy donors and patients with acquired blood disorders. *Blood* 114: 5473-80 (2009).
100. Yoshida, Y., Takahashi, K., Okita, K., Ichisaka, T. and Yamanaka, S., Hypoxia enhances the generation of induced pluripotent stem cells. *Cell Stem Cell* 5: 237-41 (2009).
101. Yu, J., Hu, K., Smuga-Otto, K., et al., Human Induced Pluripotent Stem Cells Free of Vector and Transgene Sequences. *Science* 324: 797-801 (2009).
102. Zhang, X., Stojkovic, P., Przyborski, S., et al., Derivation of human embryonic stem cells from developing and arrested embryos. *Stem Cells* 24: 2669-76 (2006).
103. Zhao, Y., Yin, X., Qin, H., et al., Two supporting factors greatly improve the efficiency of human iPSC generation. *Cell Stem Cell* 3: 475-479 (2008).
104. Zhou, W. and Freed, C. R., Adenoviral gene delivery can reprogram human fibroblasts to induced pluripotent stem cells. *Stem Cells* 27: 2667-2674 (2009).
105. Dimos, J. T., Rodolfa, K. T., Niakan, K. K., et al. 2008. Induced pluripotent stem cells generated from patients with ALS can be differentiated into motor neurons. *Science* 321: 1218-1221 (2008).
106. Ebert, A. D., Yu, J., Rose, F. F., Jr., et al., Induced pluripotent stem cells from a spinal muscular atrophy patient. *Nature* 457: 277-80 (2009).
107. Agarwal S, Loh Y H, McLoughlin E M, et al., *Nature* 464: 292-296 (2010).
108. Maehr, R., Chen, S., Snitow, M., et al., Generation of pluripotent stem cells from patients with type 1 diabetes. *Proc Natl Acad Sci USA* 106: 15768-15773 (2009).
109. Park, I. H., Arora, N., Huo, H., et al., Disease-specific induced pluripotent stem cells. *Cell* 134: 877-886 (2008).
110. Raya, A., Rodriguez-Piza, I., Guenechea, G., et al., Disease-corrected haematopoietic progenitors from Fanconi anaemia induced pluripotent stem cells. *Nature* 460: 53-59 (2009).
111. Nakagawa, S., et al., A new blood-brain barrier model using primary rat brain endothelial cells, pericytes and astrocytes. *Neurochem Int* 54: 253-263 (2009).
112. Nakagawa, S., et al, Pericytes from brain microvessels strengthen the barrier integrity in primary cultures of rat brain endothelial cells, *Cell Mol Neurobiol,* 27: 687-694, (2007).
113. Gaillard, P. J., et al, Establishment and functional characterization of an in vitro model of the blood-brain barrier, comprising a co-culture of brain capillary endothelial cells and astrocytes, *Eur J Pharm Sci,* 12: 215-222 (2001).
114. Schiera, G., et al, Permeability properties of a three-cell type in vitro model of blood-brain barrier, *J Cell Mol Med,* 9: 373-379 (2005).
115. Shayan, G., et al, Murine in vitro model of the blood-brain barrier for evaluating drug transport, *Eur J Pharm Sci,* 42: 148-155 (2011).
116. Dohgu, S., et al, Brain pericytes contribute to the induction and up-regulation of blood-brain barrier functions through transforming growth factor-beta production, *Brain Res,* 1038: 208-215 (2005).
117. Deli, M. A., Abraham, C. S., Kataoka, Y. & Niwa, M. Permeability studies on in vitro blood-brain barrier models: physiology, pathology, and pharmacology. *Cellular and molecular neurobiology* 25, 59-127 (2005).
118. Cowan, C. A., Atienza, J., Melton, D. A. and Eggan, K., Nuclear reprogramming of somatic cells after fusion with human embryonic stem cells. *Science* 309: 1369-73 (2005).
119. Esteban, M. A., Wang, T., Qin, B., et al., Vitamin C enhances the generation of mouse and human induced pluripotent stem cells. *Cell Stem Cell* 6: 71-79 (2009).
120. Warren L, Manos P D, Ahfeldt T, et al., Highly efficient reprogramming to pluripotency and directed differentiation of human cells with synthetic modified mRNA. *Cell Stem Cell*. 7: 618-630 (2010).
121. Revazova, E. S., Turovets, N. A., Kochetkova, O. D., et al., Patient-specific stem cell lines derived from human parthenogenetic blastocysts. *Cloning Stem Cells* 9: 432-449 (2007).
122. Capowski, E. E., Schneider, B. L., Ebert, A. D., et al., Lentiviral vector-mediated genetic modification of human neural progenitor cells for ex vivo gene therapy, *J Neurosci Methods,* 163: 338-349 (2007).
123. Krencik, R., Weick, J. P., Liu, Y., Zhang, Z. J., Zhang S. C., Specification of transplantable astroglial subtypes from human pluripotent stem cells, *Nature Biotechnol,* Epub ahead of print, May 22, 2011.

We claim:

1. A method of producing a blood brain barrier model from endothelial cells, comprising the steps of:
   (a) growing human pluripotent stem cells (hPSCs), wherein all the hPSCs are grown adherently on an extracellular matrix;
   (b) inducing differentiation of the hPSCs by culturing the hPSCs in unconditioned medium on the extracellular matrix for a sufficient amount of time until the endothelial cells form from the hPSCs and endothelial cell (EC) regions are observed, wherein no fibroblast growth factor (FGF) is present in the unconditioned medium, and
   (c) expanding the EC regions by culturing the endothelial cells in EC medium, wherein the expanded endothelial cells are glucose transporter+(GLUT-1+), platelet endothelial cell adhesion molecule+(PECAM-1+), claudin-5+, occludin+, zonula occludens-1+(ZO-1+) and p-glycoprotein+, wherein the EC regions are purified after step (b), and
   the method additionally comprising the step of growing the endothelial cells of step (c) to confluent monolayers of the endothelial cells, wherein the blood brain barrier model is obtained, wherein the blood brain barrier model is evinced by expression of various blood-brain barrier transporters.

2. The method of claim 1 additionally comprising the step of co-culturing the expanded cells of step (c) with a cell-type selected from the group consisting of astrocytes, neurons, neural progenitor cells, and pericytes.

3. The method of claim 2 wherein the co-culturing is with at least two cell types from the group.

4. A method of producing a blood brain barrier model from endothelial cells, comprising the steps of:
   (a) growing human pluripotent stem cells (hPSCs), wherein all the hPSCs are grown adherently on an extracellular matrix;
   (b) inducing differentiation of the hPSCs by culturing the hPSCs in unconditioned medium on the extracellular matrix for a sufficient amount of time until the endothelial cells form from the hPSCs and endothelial cell (EC) regions are observed, wherein no fibroblast growth factor (FGF) is present in the unconditioned medium, and
   (c) expanding the EC regions by culturing the endothelial cells in EC medium, wherein the expanded endothelial cells are glucose transporter+(GLUT-1+), platelet endothelial cell adhesion molecule+(PECAM-1+), claudin-5+, occludin+, zonula occludens-1+(ZO-1+) and p-glycoprotein+,
   the method additionally comprising the step of growing the endothelial cells of step (c) to confluent monolayers of the endothelial cells, wherein the blood brain barrier model is obtained, wherein the blood brain barrier model is evinced by expression of various blood-brain barrier transporters.

5. The method of claim 4, wherein the hPSCs are selected from the group consisting of human embryonic stem cells and induced pluripotent stem cells.

6. The method of claim 4, wherein the hPSCs are derived from a human patient.

7. The method of claim 4 wherein the expanded cells of step (c) are grown on a surface comprising extracellular matrix proteins, and wherein the expanded cells are von Willebrand factor+ and vascular endothelial (VE)-cadherin+.

8. The method of claim 4, wherein the method further comprises the step of taking a trans-endothelial electrical resistance (TEER) measurement of the blood brain barrier model, wherein the TEER measurement is $\geq 800 \ \Omega \times cm^2$.

* * * * *